(12) United States Patent
Veige et al.

(10) Patent No.: US 10,731,164 B2
(45) Date of Patent: Aug. 4, 2020

(54) APTAMER CONJUGATES WITH N-HETEROCYCLIC CARBENE METAL COMPLEXES FOR TARGETED DRUG DELIVERY

(71) Applicant: University of Florida Research Foundation, Inc., Gainesville, FL (US)

(72) Inventors: Adam S. Veige, Gainesville, FL (US); Mary E. Garner, Oakland, CA (US); Weijia Niu, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 511 days.

(21) Appl. No.: 15/397,231

(22) Filed: Jan. 3, 2017

(65) Prior Publication Data

US 2017/0107516 A1    Apr. 20, 2017

Related U.S. Application Data

(63) Continuation-in-part of application No. PCT/US2015/039014, filed on Jul. 2, 2015.

(60) Provisional application No. 62/019,960, filed on Jul. 2, 2014.

(51) Int. Cl.
| | | |
|---|---|---|
| *A61K 35/35* | (2015.01) | |
| *C12N 5/077* | (2010.01) | |
| *C12N 15/115* | (2010.01) | |
| *A61K 47/54* | (2017.01) | |
| *A61K 31/555* | (2006.01) | |

(52) U.S. Cl.
CPC .......... *C12N 15/115* (2013.01); *A61K 31/555* (2013.01); *A61K 47/549* (2017.08); *C12N 2310/16* (2013.01); *C12N 2310/351* (2013.01)

(58) Field of Classification Search
None
See application file for complete search history.

(56) References Cited

U.S. PATENT DOCUMENTS

| | | |
|---|---|---|
| 2007/0110827 A1 | 5/2007 | Murthy |
| 2010/0234450 A1 | 9/2010 | Schultz et al. |
| 2011/0172199 A1 | 7/2011 | Mailliet et al. |
| 2013/0324511 A1 | 12/2013 | Che et al. |
| 2014/0142080 A1 | 5/2014 | Che et al. |

OTHER PUBLICATIONS

Mullick et al., Dalton Trans., Feb. 19, 2013, DOI: 10.1039/c3dt32844a (Year: 2013).*
Huang et al. ("Huang"; ChemBioChem, 2009, 10:862-868 (Year: 2009).*
Liu et al., Chem. Soc. Rev., 2013,42:755-773 (Year: 2013).*
Oehninger et al., Dalton Trans. 2013, 42:3269-3284.*
McGinely, N.L. et al., DNA-based aptamer fails as simultaneous cancer targeting agent and drug delivery vehicle for a phenanthroline-based platinum(II) complex, *Journal of Inorganic Biochemistry*, 2013, pp. 124-130, vol. 128.
Sun, R.W-Y. et al., "Luminescent cyclometalated platinum(II) complexes containing N-hetercyclic carbene ligands with potent in vitro and in vivo anti-cancer properties accumulate in cytoplasmic structures of cancer cells," *Chemical Science*, 2011, pp. 728-736, vol. 2.
Weaver, J. et al., Cytotoxicity of Gold(I) N-Heterocyclic Carbene Complexes Assessed by Using Human Tumor Cell Lines, *Chem. Eur. J.*, 2011, pp. 6620-6624, vol. 17.
Zhu, G. et al., "Nucleic acid aptamers: an emerging frontier in cancer therapy," *Chem. Commun.*, 2012, pp. 10472-10480, vol. 48.
"Easy molecular bonding crosslinking technology," Crosslinking Technical Handbook, *Thermo Scientific*, 2012, pp. 1-56.
Marolt U. et al., Generating Aptamers for Cancer Diagnosis and Therapy, *Clin Exp Pharamacol.*, 2012, pp. 1-8, vol. 2, Issue 2.
Meyer, C. et al., "Cell-Specific Aptamers as Emerging Theraputics," *Journal of Nucleic Acids*, 2011, pp. 1-19, vol. 2011, Article ID 904750.
Medvetz, D.A. et al., "Anticancer Activity of Ag(I) N-Heterocyclic Carbene Complexes Derived from 4,5-Dichloro-1H-Imidazole," *Metal-Based Drugs*, 2008, pp. 1-7, vol. 2008, Article ID 384010.
Böhler, C. et al., "Synthesis of a transient tropylidene substituted N-heterocyclic carbene (tropNCH): rearrangement and formation of its gold complex," *New J. Chem.*, 2002, pp. 1291-1295, vol. 26, No. 10.
Dinda, J. et al., "Carbazole functionalized luminescent silver(I), gold (I) and gold(III)-N-hetercyclic carbene complexes: a new synthetic disproportionation approach towards Au(I)-NHC to provide Au(III)-NHC," *New J. Chem.*, 2013, pp. 431-438, vol. 37, No. 2.
Moore, L.R. et al., "Synthesis and Characterization of Water-Soluble Silver and Palladium Imidazol-2-ylidene Complexes with Noncoordinating Anionic Substituents," *Organometallics*, 2006, pp. 5151-5158, vol. 25, No. 21.

(Continued)

*Primary Examiner* — James D Schultz
(74) *Attorney, Agent, or Firm* — Marshall, Gerstein & Borun LLP

(57) ABSTRACT

An aptamer-N-heterocyclic-carbene metal complex conjugate (aptamer-NHCM conjugate) or an aptamer-bis-N-heterocyclic-carbene metal complex conjugate (aptamer-bis-NHCM conjugate) includes an aptamer coupled through a hydrolytically stable bond to an N-heterocyclic-carbene metal complex (NHCM) or a bis-N-heterocyclic-carbene metal complex (bis-NHCM). The aptamer-NHCM conjugate is prepared where the chosen aptamer displays selective binding to a cell specific receptor, such that the cytotoxic NHCM can be directed specifically to cells responsible for a target disease (e.g., a specific cancer type). A method of preparing the aptamer-N-heterocyclic-carbene metal complex conjugate involves installing a coupling group to an N-heterocyclic-carbene metal complex that can specifically bond with a functional group on an aptamer; the bond, covalent or non-covalent, is stable hydrolytically in the absence of an environment that promotes intentional cleavage of the bond.

18 Claims, 25 Drawing Sheets

Specification includes a Sequence Listing.

(56) References Cited

OTHER PUBLICATIONS

Özdemir, I. et al., "Synthetic and antimicrobial studies on new gold(I) complexes of imidazolidin-2-ylidenes," *Appl. Organometal. Chem.*, 2004, pp. 318-322, vol. 18, No. 7.

Özdemir, I. et al., Gold (I) Complexes of N-Heterocyclic Carbene Ligands Containing Benzimidazole: Synthesis and Antimicrobial Activity, *Molecules,* 2010, pp. 2203-2210, vol. 15, No. 4.

Poyatos, M. et al., "New Rh(I) and Rh(III) Bisimidazol-2-ylidene Complexes: Synthesis, Reactivity, and Molecular Structures," *Inorg. Chem.*, 2003, pp. 2572-2576, vol. 42, No. 8.

Raubenheimer, H.G. et al., "Carbene complexes derived from lithiated heterocycles, mainly azoles, by transmetallation," *Journal of Organometallic Chemistry,* 2001, pp. 170-181, vol. 1.

Shangguan, D. et al., "Aptamers Evolved from Cultured Cancer Cells Reveal Molecular Differences of Cancer Cells in Patient Samples," *Clinical Chemistry,* 2007, pp. 1153-1155, vol. 53, No. 6.

Wang, H.M.J. et al., "Facile Synthesis of Silver(I)-Carbene Complexes. Useful Carbene Transfer Agents," *Organometallics,* 1998, pp. 972-975, vol. 17, No. 5.

Zou, T. et al., "Gold (III) Complexes Containing N-Heterocyclic Carbene Ligands: Thiol "Switch-on" Fluorescent Probes and Anti-Cancer Agents," Angewandte Communications, 2013, pp. 2930-2933, vol. 52.

\* cited by examiner

| 1 | 2 | 3 | 4 |
|---|---|---|---|
| IC$_{50}$= 0.21 uM (MDA MB231) Breast Carcinoma | IC$_{50}$= 0.90 uM (MDA MB231) Breast Carcinoma | IC$_{50}$= 0.92 uM (MDA MB231) Breast Carcinoma | IC$_{50}$= 4.6 uM (MCF-7) Breast Carcinoma |
| IC$_{50}$= 0.75 uM (LNCaP) Prostate Carcinoma | IC$_{50}$= 1.40 uM (LNCaP) Prostate Carcinoma | IC$_{50}$= 1.90 uM (LNCaP) Prostate Carcinoma | IC$_{50}$= 6.4 uM (HT-29) Colon Carcinoma |

IC$_{50}$= 8.7 uM (HeLa)
Cervical Carcinoma
IC$_{50}$= 4.6 uM (HEK)
Embryonic kidney

| | MDA-MB-231 (breast cancer cell) | DU145 (Prostate cancer cell) | HeLa (Cervical cancer cell) | HEK293 (Human kidney cell) | HU1545 (Human liver cell) |
|---|---|---|---|---|---|
| NHC-Au29 | 21.1±1.06 | 26.4±1.79 | 18.8±0.77 | 38.7±1.18 | 22.3±1.41 |
| AS1411-29 | 3.77±0.81 | 3.92±0.70 | 2.04±0.16 | >10 | >10 |
| AS1411 | >10 | >10 | >10 | >10 | >10 |
FIG. 23
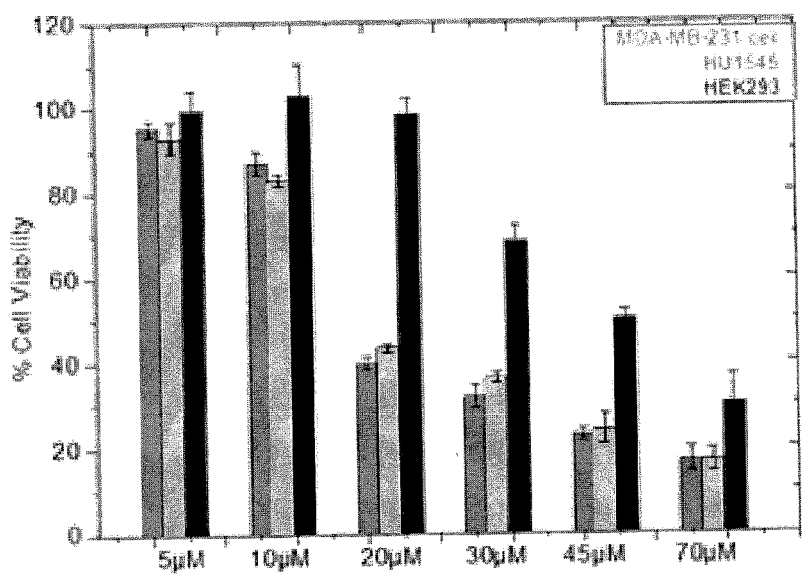
FIG. 24A
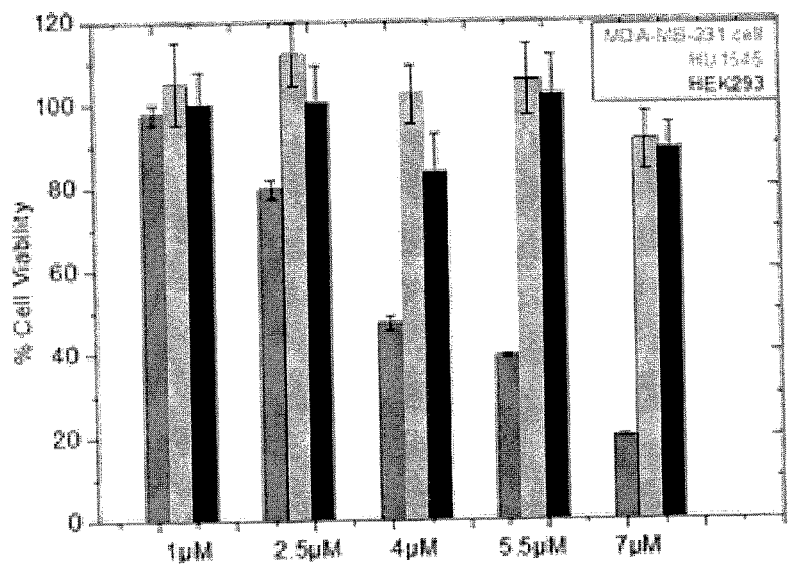
FIG. 24B

SEQUENCE LISTING

<160> NUMBER OF SEQ ID NOS: 2

<210> SEQ ID NO 1
<211> LENGTH: 41
<212> TYPE: DNA
<213> ORGANISM: Artificial Sequence
<220> FEATURE:
<223> OTHER INFORMATION: Chemically synthesized sgc8c primer

<400> SEQUENCE: 1
atctaactgc tgcgccgccg ggaaaatact gtacggttag a         41

<210> SEQ ID NO 2
<211> LENGTH: 26
<212> TYPE: DNA
<213> ORGANISM: Artificial Sequence
<220> FEATURE:
<223> OTHER INFORMATION: Chemically synthesized AS1411 aptamer

<400> SEQUENCE: 2
ggtggtggtg gttgtggtgg tggtgg         26

APTAMER CONJUGATES WITH N-HETEROCYCLIC CARBENE METAL COMPLEXES FOR TARGETED DRUG DELIVERY

CROSS-REFERENCE TO RELATED APPLICATIONS

This application is a continuation-in-part of International patent application no. PCT/US2015/039014, filed Jul. 2, 2015, which claims the benefit of U.S. Provisional Application Ser. No. 62/019,960, filed Jul. 2, 2014, the disclosures of which are hereby incorporated by reference in its entireties, including all figures, tables and drawings.

The Sequence Listing for this application is labeled "Seq-List.txt" which was created on Dec. 28, 2016 and is 1 KB. The entire contents of the sequence listing are incorporated herein by reference in its entirety.

BACKGROUND OF INVENTION

Malignant neoplasms accounted for approximately 7.6 million deaths worldwide in 2008, and as the population ages, that number projects to 13.2 million by 2030. Patient responses to specific drugs vary widely and it is unreasonable to expect current drug therapies to combat the expected increase in cancer deaths. Personalized medicine through the use of individualized biomarkers provides a potential means of combating this problem. The biomarkers, proteins expressed by the specific cancer cell, even to the patient's particular cancer, are exploited to detect and deliver chemotherapeutics. Polyclonal and monoclonal antibodies perform this task rather well, but drawbacks exist due to the complexity and expense of antibody production in addition to the difficulty of conjugating the antibodies to active cytotoxic agents. Even if individual biomarkers can be exploited to deliver chemotherapeutic agents to the cancer cell, multiple drugs must be engineered to kill the many different varieties and patient-specific cancers.

A potential approach is to exploit cancer-specific biomarkers to deliver a drug that is highly cytotoxic to all cells in all patients. Thus, only one highly cytotoxic drug must be synthesized, as long as it is specifically delivered to the cancer cell and then excreted. Cell-specific aptamers with a high affinity for leukemia, liver, lymphoma, colon, and most recently breast cancer, are known. Aptamers are very attractive drug delivery agents because they have low molecular weights, are formed by a relatively easy and reproducible DNA synthesis, display high binding affinities and molecular specificities, are easy modified, have fast tissue penetration, have low toxicity, are tunable in binding affinity, and are easy stored. Presently a number of diagnostic kits and imaging reagents using aptamers are in production.

No single cytotoxic drug has been identified, although many metal ions are highly cytotoxic to cancer. Hence, a metal ion is an obvious choice for an all-inclusive drug candidate. Moreover, since 1935 gold complexes have served as effective aurotherapeutic agents. Auranofin, used to treat rheumatoid arthritis, is also highly active against cervical carcinoma (HeLa) cells in vitro and effective against cis-platin resistant cancer cells. Numerous derivatives of gold complexes demonstrate high activity. However, as with most heavy metals including cis-platin, accumulation in the body causes significant negative side effects. One mode of accumulation is metal ion complex degradation, whereby a metal-aqua complex is formed and is difficult to excrete. Auranofin contains an Au—P($CH_2CH_3$)$_3$ gold bonded ligand, which has low stability. As a result, Auranofin accumulates in the body, which is detrimental. In contrast, N-heterocyclic carbene gold (NHCAu) complexes have the remarkable stability engendered by the Au-carbon bond. NHCAu complexes are stable towards water, acidic solutions, and heat—important qualities for a good drug candidate.

NHCAu complexes have a significant advantage because aquation and deposition of Au ions in the body can be minimized. Because NHC ligands are highly modular, the rapid and easy modification of steric and electronic properties of the metal complexes can fine-tune to the complex's cytotoxicity. Examples of NHCAu complexes that show activity are those in FIG. 1, which exhibit IC50 values as low as 0.21 µM for breast carcinoma (MDA MB231). For example, the chiral di-gold complex 5 of FIG. 1 exhibits activity towards cervical carcinoma (HeLa) with an IC50=8.7 µM. Unfortunately, the NHCAu complexes are also toxic to normal healthy cells, as in the case of 5 where an IC50=4.6 µM for healthy embryonic kidney cells (HEK) is observed.

Currently, cancer-specific aptamer-NHCAu conjugates or other aptamer-N-heterocyclic carbene metal (NHCM) conjugates are unknown but they have the potential to avoid toxicity to normal cells, while still being highly effective for the destruction of cancer cells. Thus, to prevent heavy metal accumulation in the patient and the undesired side effects, aptamer-NHCM conjugates where the gold or alternative metal ion remains attached to the aptamer are desirable.

BRIEF SUMMARY

Embodiments of the invention are aptamer-N-heterocyclic-carbene metal complex conjugates (aptamer-NHCM conjugates) and aptamer-bis-N-heterocyclic-carbene metal complex conjugates (aptamer-bis-NHCM conjugates). This design couples an aptamer to one or more N-heterocyclic-carbene metal complexes (NHCMs) and/or one or more bis-N-heterocyclic-carbene metal complexes (bis-NHCMs) through hydrolytically stable bonds between the NHCM and the aptamer. The NHCMs or bis-NHCMs can be Au, Ag, Pt, Pd, Ru, Ni, or Cu complexes that include at least one N-heterocyclic-carbene ligand of the structure:

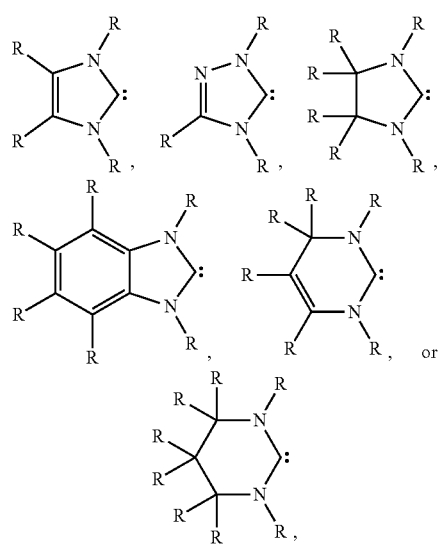

wherein R-groups are independently H, $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene and optionally substituted or multiply substituted with any of Cl, Br, I, F, OH, $R'_2N$, $R'SO_2$, $R'SO$, $R'S$, $R'_3Si$, $R'O$, $NH_2$, C(O)OH, $N_3$, C≡CH, vicinal disubstituted with C(O)OC(O), a cyclic conjugated diene, any salts derived therefrom or any condensation or addition derivative substituent therefrom, wherein R' can be $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene, wherein at least one of the R groups of the N-heterocyclic-carbene comprises the condensation or addition derivative substituent comprising the coupling unit that forms the stable bond between the N-heterocyclic-carbene metal complex and the aptamer, wherein the condensation or addition derivative substituent is derived from condensation or addition of a —$NH_2$ and —C(O)OH, —$N_3$, and —C≡CH; —$NH_2$ and vicinal disubstituted —C(O)OC(O)—, or homocyclic or heterocyclic conjugated diene and —C≡CH or —HC≡$CH_2$. The aptamer is chosen to bind to a cancer cell specific receptor, such as a G-protein coupled receptor, epidermal growth factor receptor, tyrosine kinase receptor mutation variant III, or protein tyrosine kinase receptor 7. The coupling unit can include an amide —NHC(O)—, a 1,4-substituted triazole —$N_3C_2H$—; an imide [—C(O)$]_2$N—, a bicycle[2.2.1]heptane —$C_7H_8$—, a substituted bicycle[2.2.1]heptane, a 7-oxabicyclo[2.2.1]heptane —$C_6H_6O$—, a substituted 7-oxabicyclo[2.2.1]heptane, a 7-azabicyclo[2.2.1]heptane —$C_6H_7N$—, a substituted 7-azabicyclo[2.2.1]heptane, or a succinimide thioether.

Additionally or alternatively, a bis-N-heterocyclic-carbene metal complex can be included such that a plurality of N-heterocyclic-carbene ligands complex one or more metals and are coupled to an aptamer. N-heterocyclic-carbene ligands can be coupled through a framework that limits the degree of conformational freedom and disposes the ligands in a favorable orientation to complex a single metal ion. The framework can be, but is not necessarily, a portion of the coupling unit for attachment of the aptamer. In an embodiment of the invention, the framework and N-heterocyclic-carbenes can be a trans-9,10-dihydro-9,10-ethanoanthracene-11,12-di-N-heterocyclic-carbene.

An embodiment of the invention is the treatment of a disease by administering the aptamer-NHCM conjugate in a pharmaceutically effective amount to a patient with a cancer or a microbial infection. The aptamer-NHCM conjugate binds to the disease causing cells via the specific cell surface receptor present on the disease causing cells.

BRIEF DESCRIPTION OF DRAWINGS

FIG. 23 is a table of MTS cell proliferation assay results of cancer cell lines and normal cell lines after treated with cationic NHC—Au complex 29 and 32 (AS1411-29) conjugate, where AS1411 aptamer was used as a control.

FIG. 24A shows a bar chart that compares the cell viability of MDA-MB-231, HU1545 and HEK293 after incubation with NHC—Au complex 29.

FIG. 24B shows a bar chart that compares the cell viability of MDA-MB-231, HU1545 and HEK293 after incubation with conjugate 32 (AS1411-29).

BRIEF DESCRIPTION OF THE SEQUENCES

SEQ ID NO: 1: Sequence of sgc8c, an example of an aptamer.

SEQ ID NO: 2: Sequence of AS1411, an example of an aptamer

DETAILED DISCLOSURE

Embodiments of the invention are aptamer-N-heterocyclic-carbene metal complex conjugates (aptamer-NHCM conjugates) or aptamer-bis-N-heterocyclic-carbene metal complex conjugates (aptamer-bis-NHCM conjugates). These include aptamer-N-heterocyclic-carbene gold complex conjugates (aptamer-NHCAu conjugates) or other aptamer-NHCM metal complex conjugates, for targeting cancer cells. The aptamer-NHCM conjugates are constructed to ensure that the gold or alternative metal ion complex remains intact and bound to the aptamer. In this manner, the decomposition of the metal complex is avoided along with heavy metal accumulation side effects. The conjugation of the gold, or other metal ion complex, to the aptamer is through an inert and highly stable bond (e.g., an amide bond). An embodiment of the invention involves a method to couple an aptamer containing or adapted to contain a functionality that can bond with a NHCM complex containing the complementary functionality. In one embodiment of the invention, the aptamer functionality is an amine and the complementary functionality of the NHCM complex is a carboxylic acid. In another embodiment of the invention, the NHCM complex has amine functionality and an aptamer has a carboxylic acid coupling functionality. In other embodiments of the invention, the aptamer is modified to attach a complementary functionality onto the aptamer and the NHCM complex is equipped with a complementary functionality for the formation of at least one bond by a "click" reaction or other high conversion addition or condensation reactions. For example, the functionalities can be —$N_3$ and —C≡CH for a Huisgen cycloaddition, an -ene or an -yne, a conjugated diene, a cyclic diene or a heterocyclic diene for a Diels-Alder cycloaddition, a primary amine and a dicarboxylic acid anhydride for an imidization, a maleimide and a thiol for a succinimide thioether, or any other complementary reactive functionalities for a high yield, stoichiometric reaction to couple the units upon combining the aptamer and NHCM or bis-NHCM.

Figure 2:
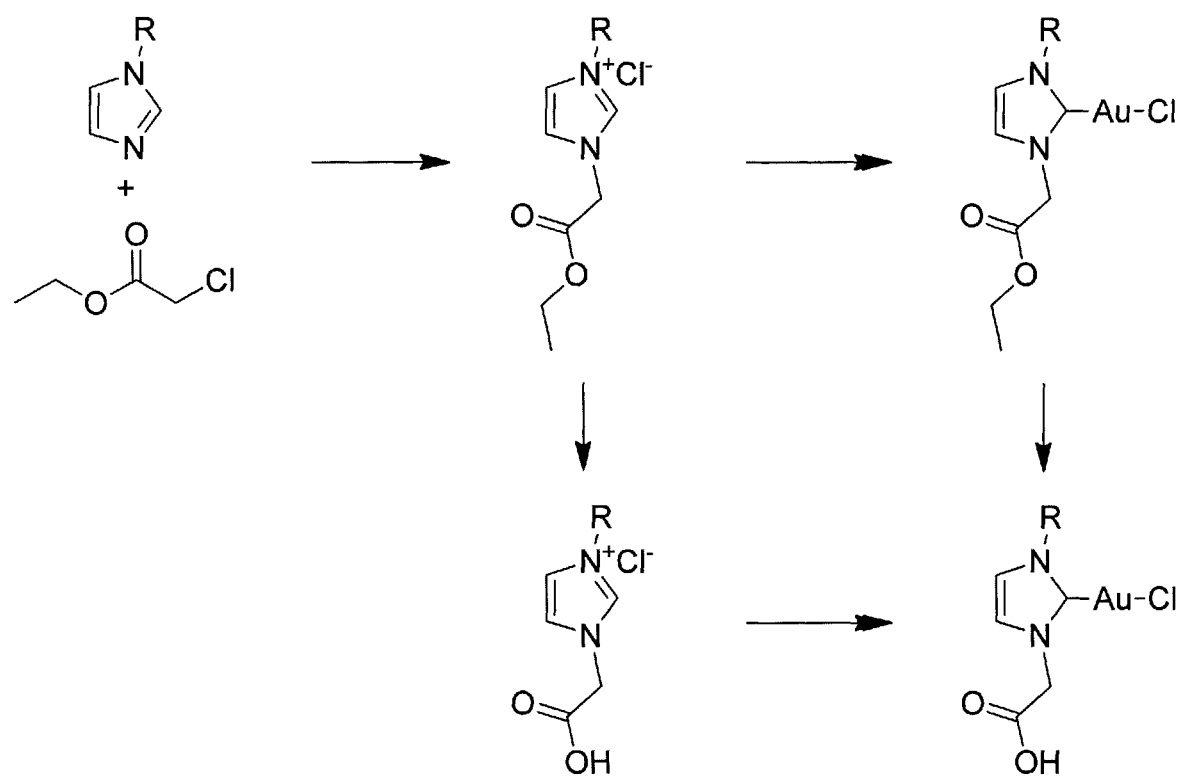
FIG. 2 shows reaction schemes to produce a carboxylic acid containing NHC-gold complex capable of conjugating to an aptamer, according to an embodiment of the invention.

FIG. 2 shows two alternative reactions sequences to synthesize an exemplary carboxylic acid containing NHC-gold complex where an alkyl imidazole reacts with a chloro substituted ester to yield an imidazolium salt in high yield. Subsequently, metalation followed or preceded by ester hydrolysis forms the NHCAu complex with a carboxylic acid group. Other N-heterocyclic carbenes can be substituted for the exemplary imidazole containing carbene Au complex, shown for an exemplary NHCAu complex in FIG. 2, or used to prepare any alternative NHC-metal (NHCM) complex and ultimately the aptamer-NHCM conjugates. The carbene can be of the structure:

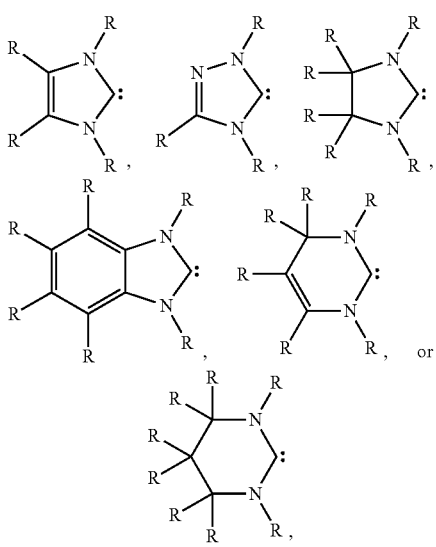

where R-groups are independently H, $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene and optionally substituted or multiply substituted with any of Cl, Br, I, F, OH, $R'_2N$, $R'SO_2$, $R'SO$, $R'S$, $R'_3Si$, $R'O$, $NH_2$, C(O)OH, $N_3$, C≡CH, vicinal disubstituted with C(O)OC(O), a cyclic conjugated diene, or any salts derived therfrom, wherein R' can be $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene, where, optionally, one of the R groups of one of the N-heterocyclic-carbenes contains the requisite coupling functional group to a complementary functionality necessary for covalent attachment to the aptamer, where the coupling functional group is —$NH_2$, —C(O)OH, —$N_3$, —C≡CH; vicinal disubstituted —C(O)OC(O)—, or homocyclic or heterocyclic conjugated diene, where R and R' groups are linear, branched, cyclic, polycyclic or any combination thereof, and where the N-heterocyclic-carbene is achiral, racemic mixture, partially resolved enantiomer, resolved enantiomer, or a mixture of diastereomers.

In an embodiment of the invention, the N-heterocyclic-carbene metal complex is a bis-N-heterocyclic-carbene metal complex, where a plurality of N-heterocyclic-carbene ligands and one or more metals are coupled to an aptamer. In an embodiment of the invention, N-heterocyclic-carbene ligands can be positionally fixed through a framework that limits the degree of conformational freedom to dispose the carbene ligands in a favorable orientation and proximity relative to each other to ligate a single metal ion. The framework can be, but is not necessarily, a portion of the coupling unit. In an embodiment of the invention, the framework and N-heterocyclic-carbenes can be a trans-9,10-dihydro-9,10-ethanoanthracene-11,12-di-oligomethylene-N-heterocyclic-carbene:

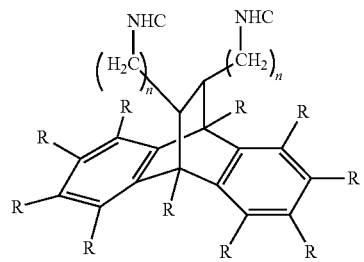

where NHC indicates any of the NHC carbenes above, independently chosen, where one of the nitrogens of each of the two NHCs is bound to the terminal methylene of the oligomethylene links of the bicyclo framework, and where n is 1 to 4. For purposes of the invention, the oligomethylene can be of a single methylene unit and does not require a plurality of methylene units to fulfill the definition of an oligomethylene. The R groups of the framework are independently defined as the R groups of the NHC carbenes, above. The trans-9,10-dihydro-9,10-ethanoanthracene-11,12-di-oligomethylene-N-heterocyclic-carbene can be a symmetric bis-NHC, such as:

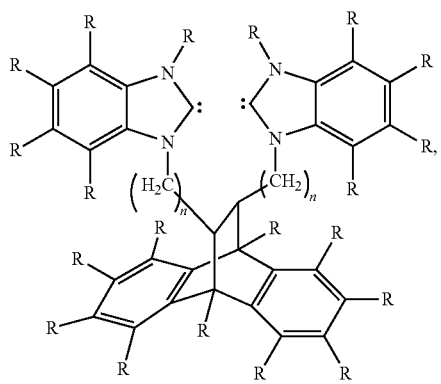

or an asymmetric bis-NHC, such as:

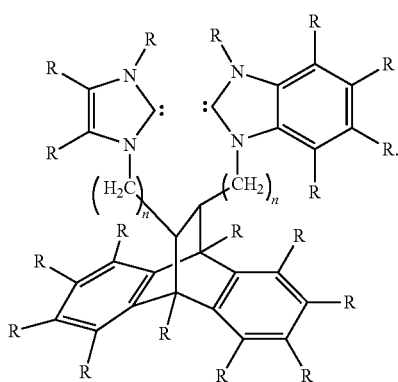

The bis-NHC metal complex, can have the structure:

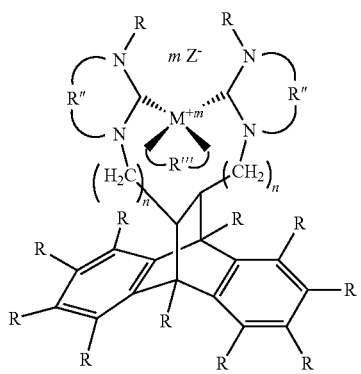

wherein n and R are defined as above, R" is independently:

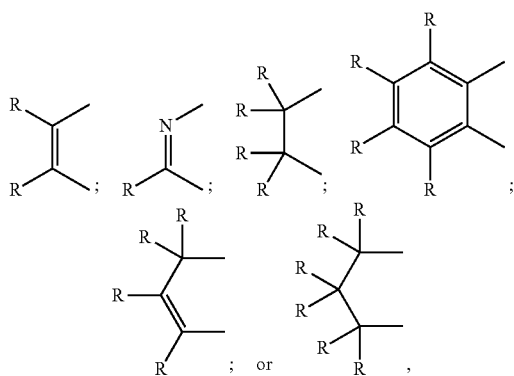

wherein anion Z is Cl⁻, Br⁻, I⁻, $BF_4^-$, $PF_6^-$, $SbF_6^-$, $^-OSO_2CF_3$, or $^-OSO_2C_6H_5$, wherein M is Au, Ag, Rh, Ir, Pd, Pt, Ru, Ni, Cu, or other transition metal, m is 0 to 3, and wherein R'" is an optional ancillary bidentate diene ligand selected from the group consisting of norbornene, substituted norbornene, 1,5-cyclooctadiene, or substituted 1,5-cyclooctadiene.

Although FIG. 2 shows an ethyl ester of the carboxylic acid, in other embodiments of the invention, alternative esters can be used, particularly those whose conversion to the carboxylic acid is carried out under mild conditions. These include, but are not limited to, benzyl and silyl esters such as trimethylsilyl, triethylsilyl, or t-butyldimethylsilyl esters, which are liberated by hydrolysis or fluoride substitution, esters of fluorinated phenols, for example pentafluorophenoxy esters, as well as alkyl esters prone to elimination by ester pyrolysis. Other embodiments of the invention can employ a precursor other than an ester that yield a carboxylic acid, for example, but not limited to, a mixed carboxylic acid anhydride, a carboxylic acid halide, or other functionality that can be hydrolyzed to form a carboxylic acid. Additional embodiments of the invention include other functionalities than those of a carboxylic acid derivative for formation of the carboxylic acid. These include, but not limited to, a nitrile, which can be hydrolyzed, or an aldehyde or alcohol which can be oxidized to form the carboxylic acid. In another embodiment of the invention, the carboxylic acid, or its carboxylate salt, can be used directly in the synthesis of the NHCAu complex without an intermediate ester or other carboxylic acid precursor functionality.

In addition to the route towards the NHCAu complex shown in FIG. 2, several alternative approaches to the synthesis of a carboxylic acid appended NHCAu complex can be carried out, including: cleavage of a C=C bond in electron rich alkenes as disclosed in Ozdemir et al., *Applied Organometallic Chemistry* 2004, 18 (7), 318-322; generation of a free carbene by deprotonation of the imidazolium precursor with a strong base as disclosed in Bohler et al., *New Journal of Chemistry* 2002, 26 (10), 1291-1295; transmetalation of a deprotonated azole followed by protonation or alkylation of the gold azolyl compound as disclosed in Raubenheimer et al., *Journal of Organometallic Chemistry* 2001, 617 (1), 170-181; in situ deprotonation of an imidazolium salt with a weak base as disclosed in Poyatos et al., *Inorganic Chemistry* 2003, 42 (8), 2572-2576; and transmetalation from a silver-NHC complex prepared by a reaction of an imidazolium precursor with $Ag_2O$ as disclosed in Wang et al., *Organometallics* 1998, 17 (5), 972-975 and Ozdemir et al., *Molecules* 2010, 15 (4), 2203-2210, all of these references are incorporated herein by reference.

Figure 3:
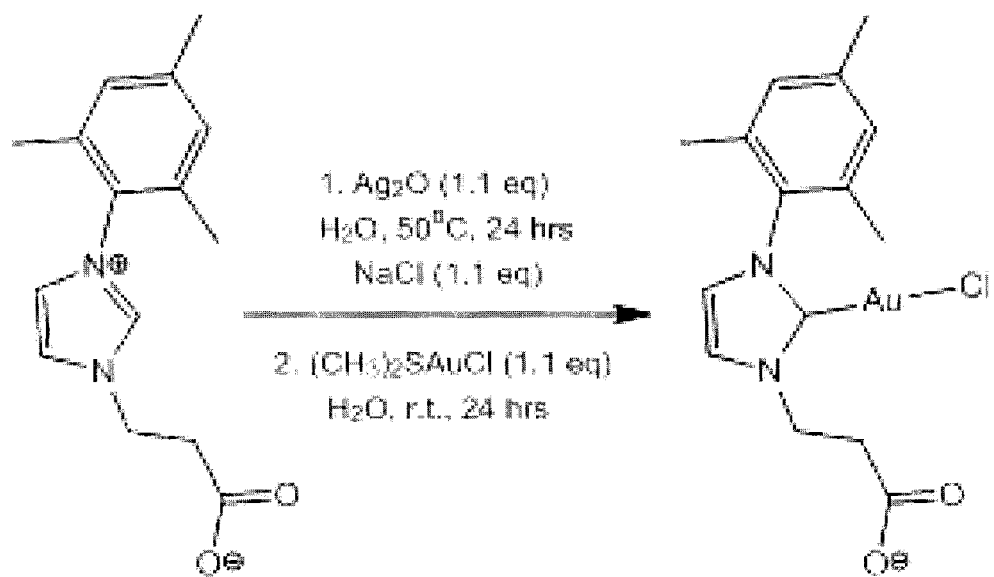
FIG. 3 shows a reaction scheme to generate a silver salt from a carboxylate alkyl substituted imidazole zwitterion and converting the NHCAg complex into the NHCAu complex prior to conjugation with an aptamer, according to an embodiment of the invention.

Of these routes, a gold(I)-NHC complex is readily synthesized via transmetalation from a corresponding silver(I)-NHC complex or bis-NHC-silver(I) halide salt by treatment with an appropriate gold(I) source. Carboxylate functionalized silver(I)-NHC complexes can be readily prepared by the method disclosed in Moore et al., *Organometallics* 2006, 25 (21), 5151-5158, which is incorporated herein. FIG. 3 shows a reaction scheme to generate a silver salt from a carboxylic acid alkyl substituted imidazole zwitterion and subsequently convert the NHCAg complex to the NHCAu complex.

An NHCAu complex can comprise any of the structures:

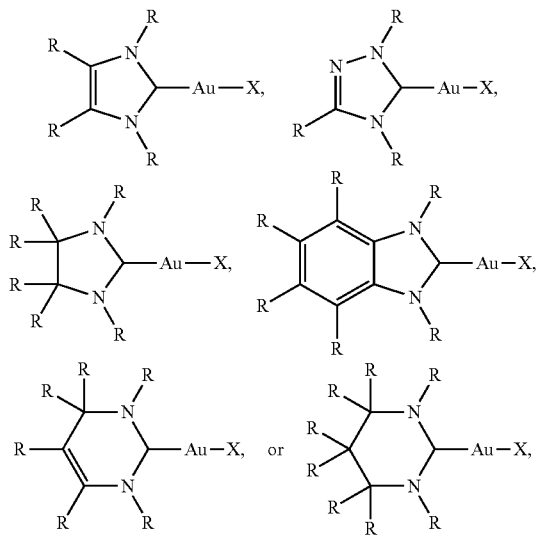

and a bis-NHCAu complex can comprise any of the structures:

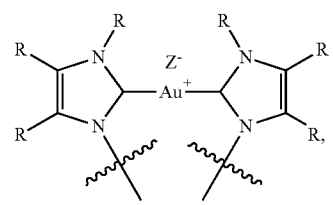

-continued
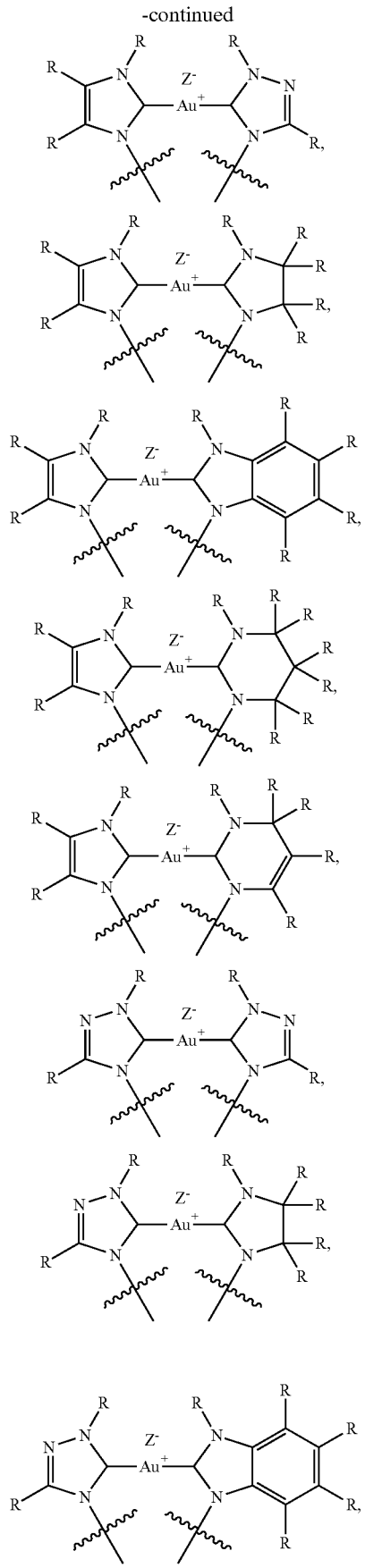
-continued
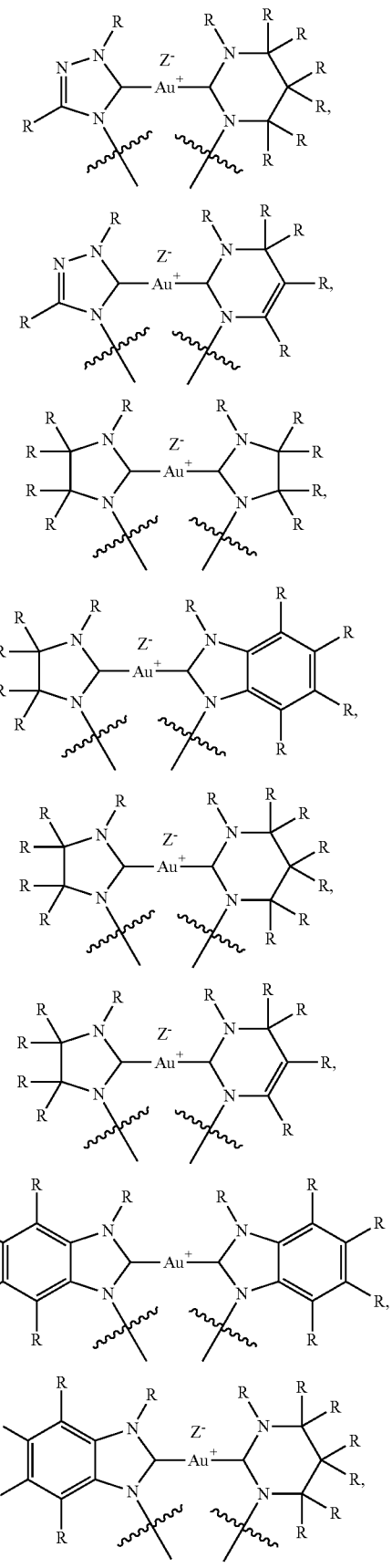

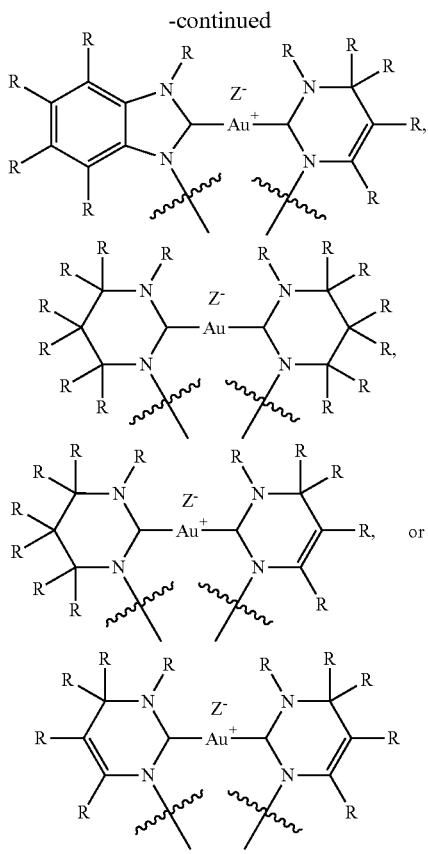

wherein X is Cl, Br, I or OH, Z is Cl$^-$, Br$^-$, I$^-$, BF$_4^-$, PF$_6^-$, SbF$_6^-$, $^-$OSO$_2$CF$_3$, or $^-$OSO$_2$C$_6$H$_5$, and, independently, R-groups are independently H, C$_1$-C$_{18}$ alkyl, C$_2$-C$_{18}$ alkenyl, C$_2$-C$_{18}$ alkynyl, C$_6$-C$_{14}$ aryl, C$_7$-C$_{18}$ arylalkyl, C$_8$-C$_{18}$ arylalkenyl, C$_8$-C$_{18}$ arylalkynyl, C$_1$-C$_{18}$ alkoxy, C$_6$-C$_{14}$ aryloxy, C$_7$-C$_{18}$ arylalkyloxy, C$_2$-C$_{18}$ alkenyloxy, C$_2$-C$_{18}$ alkynyloxy, C$_8$-C$_{18}$ arylalkenyloxy, C$_8$-C$_{30}$ arylalkynyloxy, C$_2$-C$_{30}$ alkylester, C$_7$-C$_{15}$ arylester, C$_8$-C$_{30}$ alkylarylester, C$_3$-C$_{18}$ alkenylester, C$_3$-C$_{18}$ alkynylester, C$_3$-C$_{18}$ di- or poly-ether, C$_3$-C$_{18}$ di- or poly-etherester, C$_3$-C$_{18}$ di- or poly-ester, C$_3$-C$_{18}$ di- or poly-amine, C$_4$-C$_{18}$ di- or poly-ene and optionally substituted or multiply substituted with any of Cl, Br, I, F, OH, R'$_2$N, R'SO$_2$, R'SO, R'S, R'$_3$Si, R'O, NH$_2$, C(O)OH, N$_3$, C≡CH, vicinal disubstituted with C(O)OC(O), a cyclic conjugated diene, any salts derived therefrom or any condensation or addition derivative substituent therefrom, wherein R' can be C$_1$-C$_{18}$ alkyl, C$_2$-C$_{18}$ alkenyl, C$_2$-C$_{18}$ alkynyl, C$_6$-C$_{14}$ aryl, C$_7$-C$_{18}$ arylalkyl, C$_8$-C$_{18}$ arylalkenyl, C$_8$-C$_{18}$ arylalkynyl, C$_1$-C$_{18}$ alkoxy, C$_6$-C$_{14}$ aryloxy, C$_7$-C$_{18}$ arylalkyloxy, C$_2$-C$_{18}$ alkenyloxy, C$_2$-C$_{18}$ alkynyloxy, C$_8$-C$_{18}$ arylalkenyloxy, C$_8$-C$_{30}$ arylalkynyloxy, C$_2$-C$_{30}$ alkylester, C$_7$-C$_{15}$ arylester, C$_8$-C$_{30}$ alkylarylester, C$_3$-C$_{18}$ alkenylester, C$_3$-C$_{18}$ alkynylester, C$_3$-C$_{18}$ di- or poly-ether, C$_3$-C$_{18}$ di- or poly-etherester, C$_3$-C$_{18}$ di- or poly-ester, C$_3$-C$_{18}$ di- or poly-amine, C$_4$-C$_{18}$ di- or poly-ene, wherein at least one of the R groups of the N-heterocyclic-carbene comprises the condensation or addition derivative substituent that comprises the coupling unit with the stable bond between the N-heterocyclic-carbene metal complex and the aptamer, where the condensation or addition derivative substituent is derived from condensation or addition of a —NH$_2$ and —C(O)OH, —N$_3$ and —C≡CH; —NH$_2$ and vicinal disubstituted —C(O)OC(O)—, homocyclic or heterocyclic conjugated diene and —C≡CH or —HC═CH$_2$, or —SH and a maleimide, wherein R and R' groups are linear, branched, cyclic, polycyclic or any combination thereof, and wherein the N-heterocyclic-carbene is achiral, a racemic mixture, partially resolved enantiomer, resolved enantiomer, resolved diastereomers, or a mixture of diastereomers. The undefined bonding to a nitrogen of the N-heterocyclic carbene can be to an R group or can be attached to a framework, such as to the terminal position of the oligomethylene trans-9,10-dihydro-9,10-ethanoanthracene-11,12-di-oligomethylene-N-heterocyclic-carbene.

In other embodiments of the invention, the Au metal can be substituted by Ag, Pt, Pd, Ru, Ni, or Cu, where the additional X, Z$^-$, and/or NHC ligands lacking a site for coupling with an aptamer can be included in the complex as required by the oxidation state of the metal ion in the complex, as the metal ion can be in any oxidation state.

Aptamers are polynucleotide or polypeptide molecules that bind to a specific target molecule. Non-limiting examples of aptamers include: DNA aptamers; RNA aptamers; XNA (nucleic acid analogs or artificial nucleic acids) aptamers; and polypeptide aptamers. Examples of XNA include, but are not limited to, polypeptide nucleic acid (PNA), morpholino and locked nucleic acid (LNA), glycol nucleic acid (GNA), and threose nucleic acid (TNA).

NHCM can be conjugated to aptamers in a covalent or a non-covalent manner. NHCM can be covalently conjugated to aptamers directly or via molecular linkers. Various molecular linkers are known to a person of ordinary skill in the art, and certain non-limiting examples are described in "Easy molecular bonding crosslinking technology" published by Thermo Scientific (2012), the contents of which are herein incorporated by reference in its entirety.

In an embodiment of the invention, the covalent bond between the aptamer and NHCM is acid labile so that the covalent bond is broken between the NHCM and the conjugated aptamer as the NHCM and aptamer are internalized by the target cells and subjected to the acidic environment of the endosomes, thereby releasing the NHCMs into the target cells. An example of acid labile cross-linking involves the use of N-(Epsilon-Maleimidocaproic Acid) hydrazide to conjugate NHCM with aptamers. Additional examples of acid labile covalent binding are known to a person of ordinary skill in the art and such embodiments are within the purview of the current invention.

In another embodiment of the invention, the NHCM is conjugated to the aptamer in a non-covalent manner. Non-limiting examples of non-covalent binding between NHCM and aptamers include electrostatic binding, π-binding, van der Waals interactions, and hydrophobic binding between the NHCM and the aptamers.

Aptamer conjugated NHCM complexes can be used to specifically deliver the NHCM complexes to target cells, e.g., cancer cells. The aptamers can selectively recognize target cells through specific cell surface proteins, and direct the tethered NHCM complexes to the target cells. NHCM complexes specifically targeted and delivered to target cells can kill the target cells (e.g., cancer cells), without affecting the non-targeted cells (e.g., normal cells). As such, the current invention provides compositions and methods for treating a disease, e.g., cancer, in a subject. The aptamer is capable of binding to a cell surface receptor present on a target cell. The cell surface receptor can be specific to the target cells, i.e., the cell surface receptor is present only on the surfaces of target cells and is absent from the surfaces of non-target cells, or the surface receptor is present on the surfaces of target cells at a high level and is present on the surfaces of non-target cells at a significantly lower level than that of the target cells. For example, the aptamer can bind to a cell surface receptor specific to cancer cells, i.e., a cell surface receptor which is present only on the surfaces of cancer cells and is absent from the surfaces of normal cells or is present on the surfaces of cancer cells at high level and is present on the surfaces of normal cells at a significantly lower level. The aptamer can bind to a cell surface receptor specific to an infectious agent, i.e., a cell surface receptor which is present only on the surfaces of infectious agents and is absent from the surfaces of normal cells or is present on the surfaces of infectious agents at high level and is present on the surfaces of normal cells at a significantly lower level.

Accordingly, the diseases that can be treated, according to compositions and methods of the invention, include cancer, microbial infections and other diseases where the disease causing cells exhibit presence of a specific cell surface receptor that can be exploited to target the diseased cells. Various cancers that can be treated, according to an embodiment of the invention, are well known to a person of ordinary skill in the art and such cancers are within the purview of the current invention. The microbial infections can be viral, fungal, bacterial, protozoan, or prion mediated.

To treat a disease, according to an embodiment of the invention, an aptamer can be selected for its capability to bind to all or most of the target cells in a subject without binding to all or most of the non-target cells. An aptamer can bind to a target cell through a target cell specific receptor. For example, to treat cancer according to an embodiment of the invention, the aptamer can be selected for its ability to bind to most or all of the cancer cells without binding to all or most of the normal cells through a receptor specific for cancer cells. Non-limiting examples of cancer cell specific receptors include, G-protein coupled receptors, epidermal growth factor receptor, tyrosine kinase receptor mutation variant III, and protein tyrosine kinase receptor 7. Additional examples of receptors specific to cancer cells and corresponding aptamers are well known to a person of ordinary skill in the art and such embodiments are within the purview of this invention. For example, Meyer et al. (2011), Cell-specific aptamers as emerging therapeutics, Journal of Nucleic Acids, Volume 2011, Article ID 904750, teaches cancer cell receptor specific aptamers, the contents of which are herein incorporated by reference in its entirety, particularly, page 5, section under "Cell specific aptamers for therapy" continuing on to pages 6 to 13.

Figure 1:
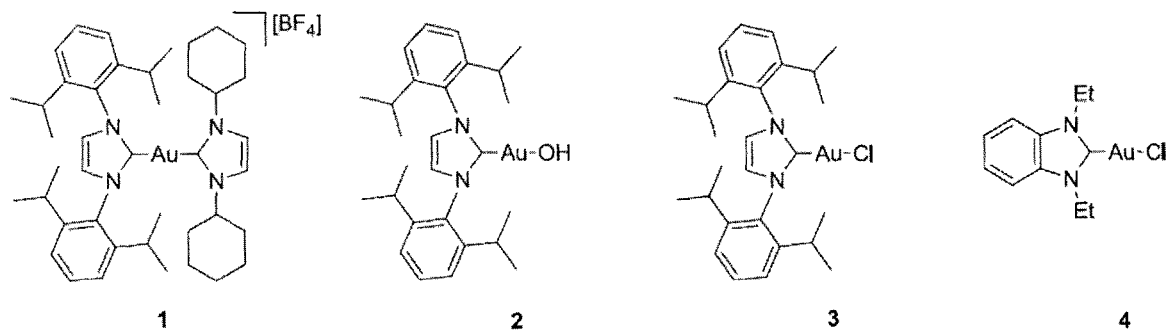
FIG. 1 shows exemplary NHCAu complexes that exhibit cytotoxicity at the micromolar level.
Figure 1:
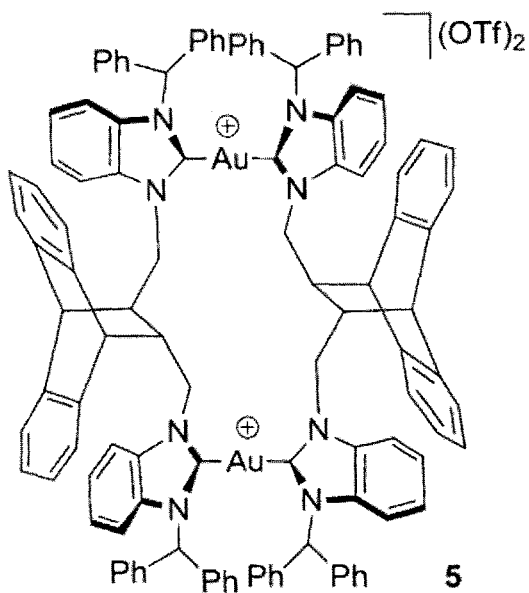

Examples of aptamers and corresponding diseases that can be treated using the aptamers are given in Marolt et al., Generating aptamers for cancer diagnosis and therapy, *Clin. Exp. Pharmacol.*, (2012) 2:111, the contents of which are herein incorporated by reference in its entirety, particularly, page 3, table 1; page 3, section under "Aptamers in cancer cell diagnostics and Treatment" continuing on to page 4; page 4, section under "Aptamers used in alimentary neoplasm, continuing on to pages 5 and 6; and FIGS. 1 and 2. Other examples of aptamers and corresponding diseases that can be treated using the aptamers are given in Meyer et al. (discussed above). A skilled artisan can identify additional diseases and corresponding aptamers that can be treated according to the compositions and methods of the current invention and such diseases are within the purview of the current invention.

The subjects that can be treated according to the methods of the current invention can be a mammal, for example, a human, porcine, canine, rodent, feline, or bovine.

The pharmaceutically effective amount of the aptamer-polynucleotide stem complex-drug conjugate depends on the type of disease to be treated and the type of drug conjugated to the complex as well as the tolerance of the subject for the treatment.

The disease treatment according to the current invention can also be administered in combination with one or more other treatments. For example, cancer in a subject can be treated by administering the NHCM-aptamer conjugate of the current invention in combination with chemotherapy and/or radiotherapy.

Figure 4:
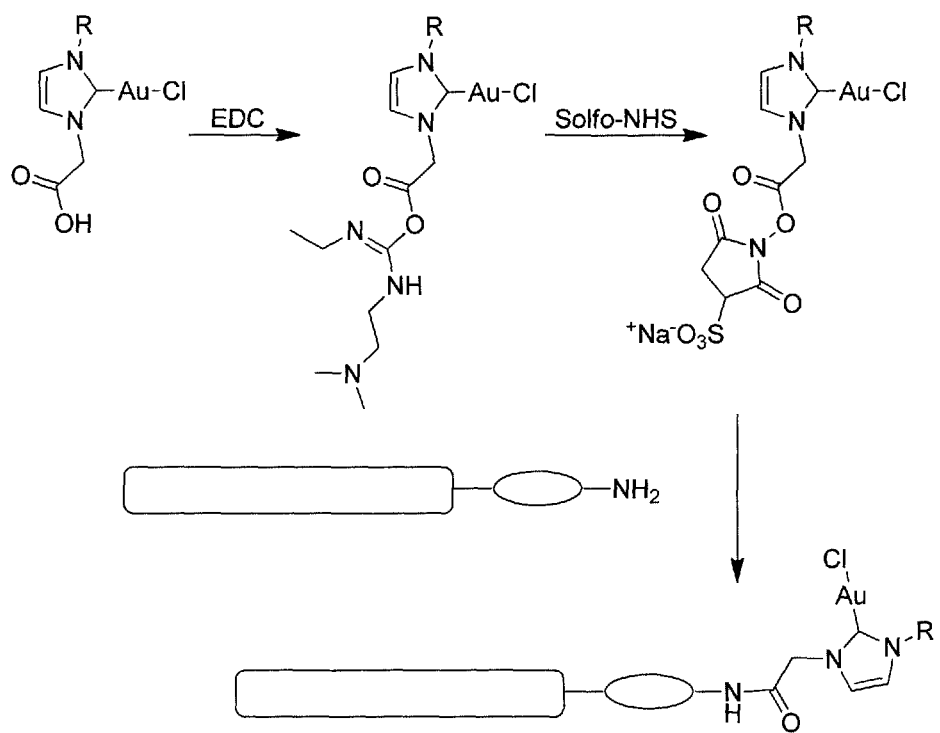
FIG. 4 shows a reaction scheme to couple the carboxylic acid containing NHC-gold complex of FIG. 2 with the coupling reagents 1-ethyl-3-[3-dimethylaminopropyl]carbodiimide hydrochloride (EDC) and the conjugation with an amine functionalized aptamer, according to an embodiment of the invention.

In an exemplary embodiment of the invention, the leukemia specific aptamer Sgce8c with a primary amine modification is coupled with a carboxylic acid functional NHCAu complex. Conjugation of a NHCM complex to the aptamer can be carried out with an aptamer, for example, but not limited to, the leukemia-specific aptamer Sgc8c (5'-ATC TAA CTG CTG CGC CGC CGG GAA AAT ACT GTA CGG TTA GA-3' SEQ ID NO: 1). For example, the coupling reagents 1-ethyl-3-[3-dimethylaminopropyl]carbodiimide hydrochloride (EDC), as shown in FIG. 4, and N-hydroxysulfosuccinimide (Sulfo-NHS) can be used to couple the carboxylic acid functionalized NHCAu complex to the primary amine modified aptamer.

Standard phosphoramidite solid phase DNA synthesis is completely automated and highly reproducible, and DNA oligonucleotides are easily purified. Aptamer synthesis by solid phase phosphoramidite chemistry is amenable to synthetic modifications. By simply inserting any commercially available phosphoramidite modified with the requisite functional group onto either the 3' or 5' end of the oligonucleotide sequence, an aptamer can be generated that is complementary for coupling to a NHCM complex.

Figure 5:
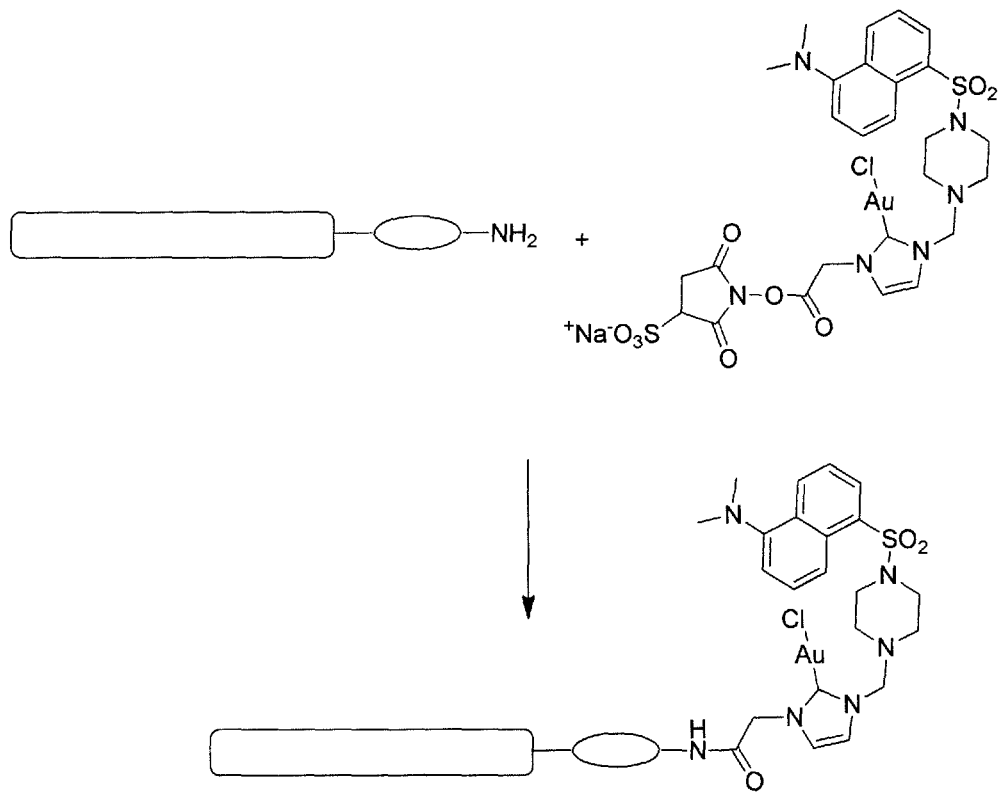
FIG. 5 shows a reaction scheme where a 1-dimethylaminonaphthalene-5-sulfonamidopolymixin (dansp) flourophore functionalized NHC-gold complex is conjugated to an amine functionalized aptamer, according to an embodiment of the invention.

In an embodiment of the invention, an NHCM complex can have an R group that is a fluorescent dye or other functionality that yields an aptamer-NHCM conjugate that can act as a delivery-therapeutic-detection agent, where the dye is a fluorophore, to facilitate in vivo detection. For example, as shown in FIG. 5, a 1-dimethylaminonaphthalene-5-sulfonamidopolymixin (dansp) flourophore functionalized NHC-gold complex can be formed and conjugated in the manner of FIG. 4 to form the aptamer-NHCAu conjugate delivery-therapeutic-detection agent. The dansp moiety fluoresces at 532 nm upon excitation at 365 nm. Other fluorescent dyes and molecules can be adapted for use as the R group, including, but not limited to, pyrenylmethyl, anthracenylmethyl, or any other fluorescent moiety. Alternatively or additionally, the NHCM complex can have an R group that comprises a polyether group or other group that can aid in crossing a cancer cell membrane and/or increasing the aptamer-NHCM complexes solubility in aqueous media.

METHODS AND MATERIALS

Compounds 1 (shown in FIG. 1) and 7 (shown in FIG. 3) were prepared according to reported procedures. Unless stated otherwise all syntheses and manipulations were performed under aerobic conditions. All starting reagents were obtained from either Sigma Aldrich or STREM chemicals and used as received without further purification. $(CH_3)_2$SAuCl, $Ag_2O$, glycine were obtained from Sigma Aldrich and used without further purification. Sgc8c-Aptamer was synthesized with a DNA synthesizer according to literature procedures.

All oligonucleotides were synthesized based on solid-phase phosphoramidite chemistry at a 1 µmol scale using the ABI3400 DNA/RNA synthesizer (Applied Biosystems, Foster City, Calif.).[1] Amine coupled at the 5'-end of oligonucleotides with 6 T group as spacer. A ProStar HPLC (Varian, Walnut Creek, Calif.) instrument with a C18 column (Econosil, 5, 250 mm) from Alltech (Deerfield, Ill.) was used to purify all fabricated DNA. The collected sequences were vacuum-dried and quantified using a Cary Bio-300 UV spectrometer (Varian Walnut Creek, Calif.).

```
Sgc8c:
                                         SEQ ID NO: 1
5'-ATC TAA CTG CTG CGC CGC CGG GAA AAT ACT GTA
CGG TTA GA-3'

AS1411:
                                         SEQ ID NO: 2
5'-GGT GGT GGT GGT TGT GGT GGT GGT GG-3'
```

All cell lines used in this research were cultured in American Type Culture Collection recommended medium, with 10% fetal bovine serum (Invitrogen, Carlsbad, Calif.) and 0.5 mg/mL penicillin-streptomycin (American Type Culture Collection) at 37° C. under a 5% $CO_2$ atmosphere. CCRF-CEM (T-cell line) and K562 (acute promyelocytic leukemia cell) were cultured in RPMI 1640 medium; MDA-MB-231 (breast cancer cells were cultured in L-15 medium; DU145 (prostate cancer cell) was cultured in EMEM medium; Hela (cervical cancer cell), HEK293 (human kidney cell) and HU1545v (human untransformed liver cell) were cultured in DMEM medium. Cells were washed before and after incubation with washing buffer [4.5 g/L glucose and 5 mM $MgCl_2$ in Dulbecco's PBS with calcium chloride and magnesium chloride (Sigma-Aldrich)]. Binding buffer was prepared by adding yeast tRNA (0.1 mg/mL; Sigma-Aldrich) and BSA (1 mg/mL; Fisher Scientific) to the washing buffer to reduce background binding. All reagents for buffer preparation and HPLC purification came from Fisher Scientific. Unless otherwise stated, all chemicals were used without further purification.

All NMR spectra were collected on either a Varian Mercury Broad Band 300 MHz or Varian Inova 500 MHz spectrometer. Chemical shifts are reported in δ (ppm) with the solvent peak referenced as an internal reference. The DOSY experiments used bipolar pulse pair stimulated echo with convection compensation. The gradient length was 1 ms and the diffusion time 100 ms; the gradient strength was arrayed in 15 steps squarely spaced from 2 to 53 Gauss/cm. Spectra were collected in 16 scans with an acquisition time of 3.6 s and a relaxation delay of 3 s.

Electrospray Ionization Mass Spectrometry (ESI-MS) data for both positive and negative modes were obtained according to the following procedure. Samples were dissolved in methylene chloride or in water and directly injected into an auto-sampler, where they were subjected to ESI with methanol as the mobile phase. Ions were detected with an Agilent 6210 TOF-MS instrument and the data was processed using MassHunterTMsoftware.

Synthesis of Compound 9

Figure 6:
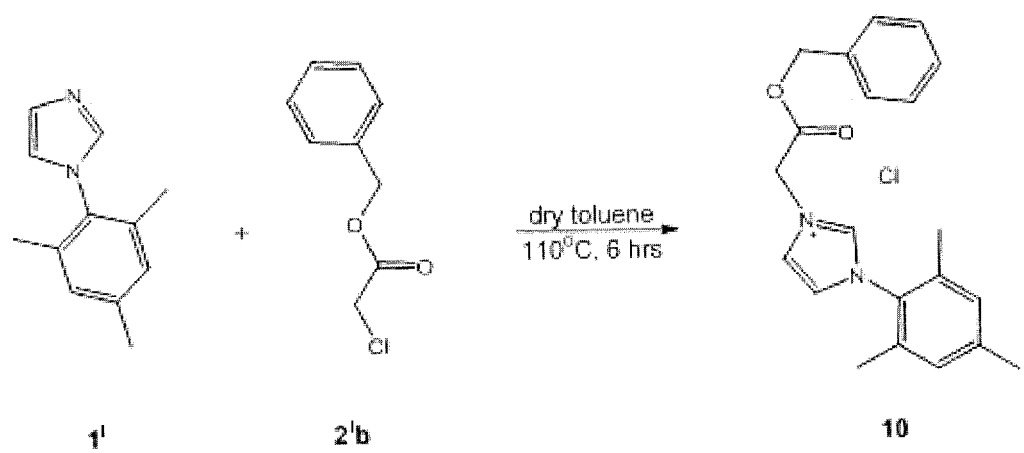
FIG. 6 shows a reaction scheme for the preparation of the imidazolium chloride salt 10 via alkylation with benzyl chloroacetate.
Figure 7:
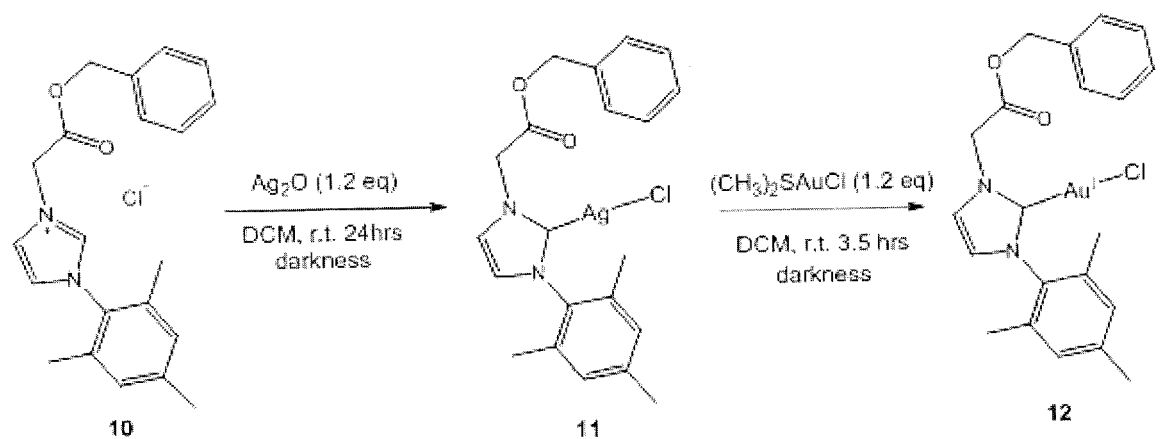
FIG. 7 shows a reaction scheme for generation of a benzyl protected silver(I) complex 11 followed by transmetalation with $(CH_3)_2SAuCl$ to yield the benzyl ester protected monocarbene gold(I)-NHC complex 12, according to an embodiment of the invention.

Bis(1-mesityl-3-(2-carboxylatoethyl)imidazol-2-ylidene)-trans-dichloride gold(III) sodium salt 9 was prepared following the procedure of Dinda et al., *New Journal of Chemistry* 2013, 37 (2), 431-438 via an in situ transmetalation reaction. To a 100 mL Schlenk flask under an atmosphere of Ar, 138.0 mg (0.534 mmol) of 7, 130.0 mg (0.561 mmol) of $Ag_2O$, a magnetic stir bar, and 20 mL of deoxygenated water were added and left to stir for 24 h at 50° C. in the dark. After 24 h, the reaction mixture was allowed to cool to ambient temperature whereupon 32.0 mg (0.548 mmol) of NaCl was added and allowed to stir for an additional 30 min at room temperature. The solution was passed through a celite pad and fine frit filter. To the filtrate, 160.0 mg (0.543 mmol) of $(CH_3)_2SAu(I)Cl$ was added and allowed to stir for 24 h at room temperature, in the dark, under an atmosphere of Ar. After 24 h, the reaction mixture was passed through a pad of celite and fine frit filter. The filtrate was reduced to 5 mL whereupon the dark purple solution was filtered to remove gold nanoparticles. The remaining solvent was removed in vacuo to give an off-white residue (62.8 mg, 30.1%). $^1$H-NMR (DMSO-$d_6$, 300 MHz). δ=7.75 (d, J=1.75 Hz, 2H), 7.38 (d, J=1.75 Hz, 2H), 6.99 (s, 4H), 4.30 (t, J=6.87 Hz, 4H), 2.41 (t, J=6.87 Hz, 4H), 2.40 (s, 6H), 1.72 (s, 12H). ESI-MS (positive ion, calculated for M=$C_{30}H_{35}AuCl_2N_4O_4$). 827.1440 m/z $[M-H+2Na]^+$, 805.1616 m/z $[M+Na]^+$, 783.1797 m/z $[M+H]^+$, 769.1852 m/z $[M-HCl+Na]^+$. ESI-MS (negative ion) 817.1222 m/z $[M+Cl]^-$, 803.1450 m/z $[M-2H+Na]^-$, 781.1640 $[M-H]^-$, 709.1415 m/z $[M-C_3H_5O_2]^-$, 637.1200 m/z $[M+H-2C_3H_5O_2]^-$, 338.8382 m/z $[AuCl_3+Cl]^-$, 266.9032 m/z $[AuCl_2-Cl]^-$ Imidazolium chloride salt 10 was prepared via alkylation with benzyl chloroacetate, as shown in FIG. 6. Generating the benzyl protected silver(I) complex 11 in situ followed by transmetalation, as shown in FIG. 7, with $(CH_3)_2SAuCl$ provides complex 12, which is confirmed by $^1$H-NMR spectroscopy. The ions detected in positive mode ESI-MS analysis support the assignment of 12 as the benzyl ester protected monocarbene gold(I)-NHC complex 12.

Figure 8:
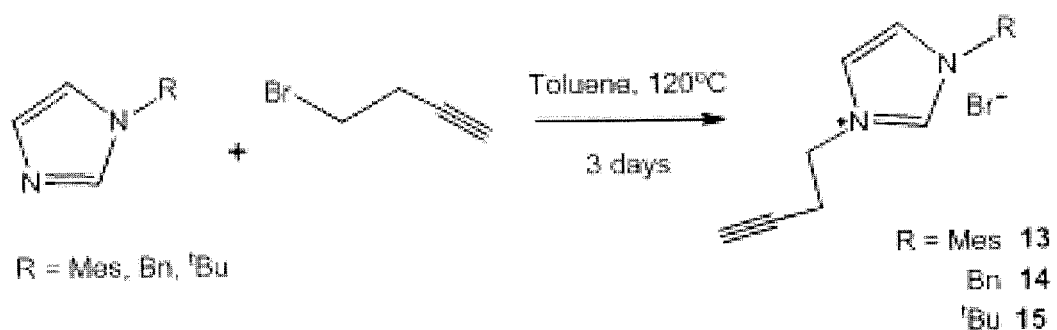
FIG. 8 shows a reaction scheme to form alkyne functionalized heterocycles 13-15.

Alkyne functionalized heterocycles 13-15, were prepared under the conditions shown in FIG. 8, where relatively harsh conditions are required to drive the reaction. Using a relatively high temperature (120° C.) and long reaction time (3 days), the method permitted the assembly of ligands 13-15 in yields of 63.4, 80.2, and <25%, respectively. $^1$H-NMR spectra of 13-15 reveal diagnostic downfield chemical shifts of 10.0-10.5 ppm, corresponding to the deshielded $C_2$ proton flanked by two nitrogen atoms of the imidazol-2-ylidene ring. $^{13}$C-NMR spectra of these ligands exhibit resonances attributable to the $C_2$ carbons between 135.7 ppm and 137.9 ppm. The terminal alkynyl protons of ligands 14 and 15 appear as triplets (J=2.2-2.7 Hz) due to long range coupling with the methylene protons distal to the heterocyclic ring and adjacent to the triple bond. This long range coupling is still present for compound 13 but is not viewable by $^1$H-NMR spectroscopy due to signal overlap with a large singlet at 2.05 ppm from the mesityl methyl groups.

Figure 9:
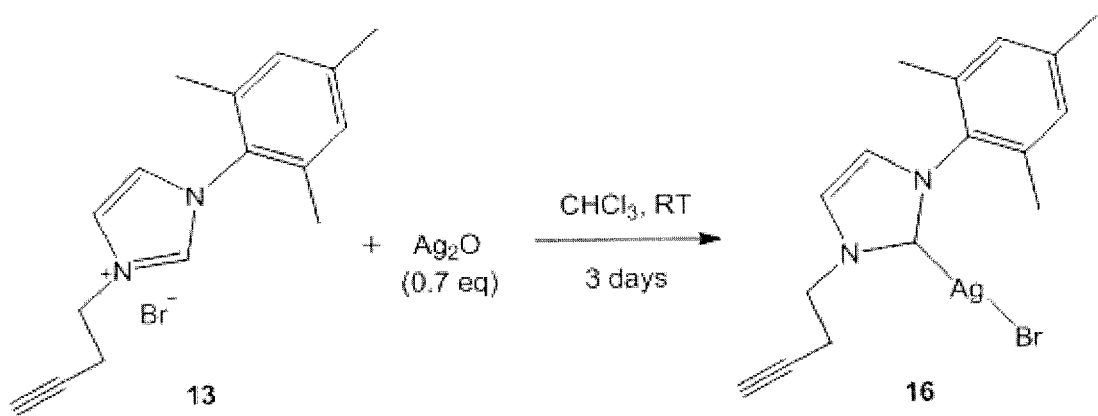
FIG. 9 shows a reaction scheme for the deprotonation and metalation of ligand 13 with silver(I)oxide to form silver complex 16.
Figure 10:
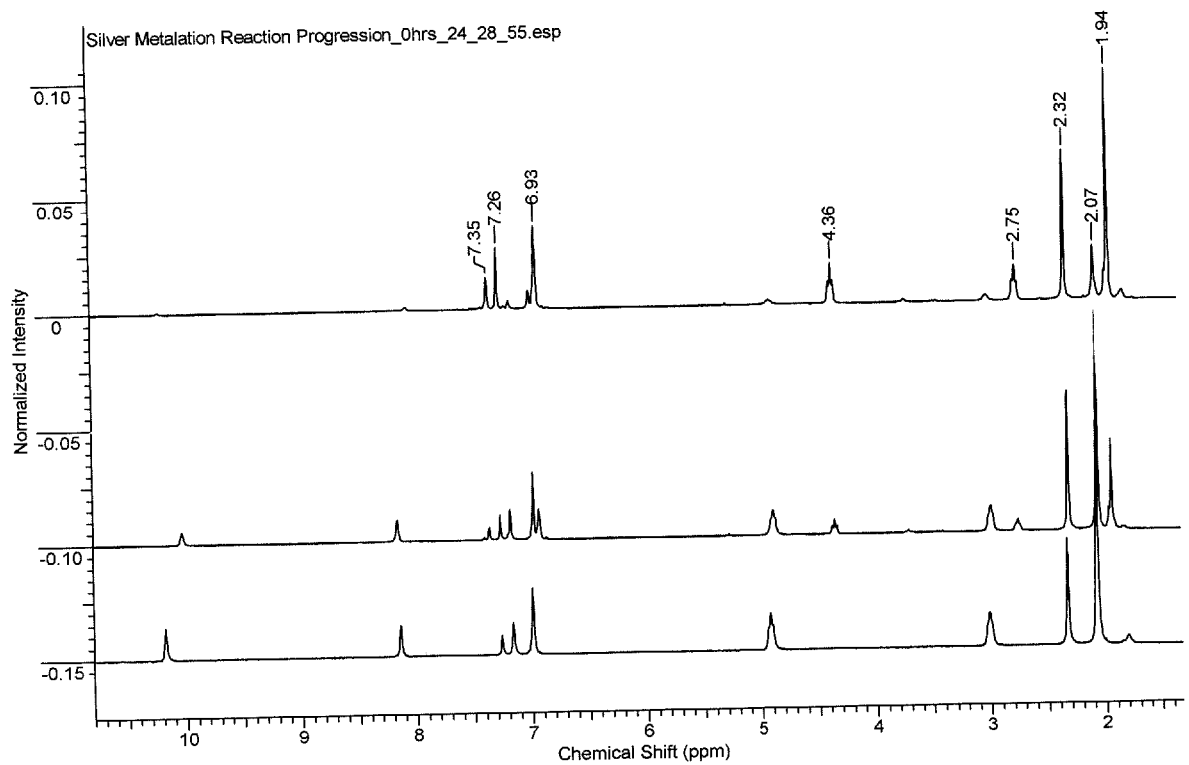
FIG. 10 shows composite $^1$H-NMR spectra of the reaction of FIG. 9 over time.

Deprotonation and metalation of ligand 13, as shown in FIG. 9, with 0.70 equivalents of silver(I)oxide required long reaction times. Aliquots of the reaction mixture taken periodically throughout the duration of the reaction and subjected to $^1$H-NMR spectroscopic analysis, as shown in FIG. 10, provided a method of monitoring the reaction progress. The ligand's $C_2$ imidazolium proton, resonating at 10.15 ppm, decreases over time concomitant with the growth of a set of resonances in the aromatic and aliphatic regions corresponding to complex 16. Total conversion of 13 to the silver(I) species 16 requires stirring at room temperature for three full days in the absence of light. Precipitation of complex 16 as a fine tan powder resulted from passing the reaction mixture through celite, reducing the filtrate by vacuum, and adding an excess of ether. The $^1$H-NMR spectrum of 16 provides evidence that the $C_2$ proton of 13 was removed. Though the lack of resonances downfield of 10 ppm in the $^1$H-NMR spectrum of 16 indicates a complex form, the weak and seemingly absent, chemical shift in the range of 170 ppm and 190 ppm (commonly reported for NHC silver(I)-carbene complexes) in the $^{13}$C-NMR spectrum of complex 16, prompted further characterization.

Data suggest that the more labile (exchanging) a silver-carbene bond is on the NMR time scale, the broader the $^{13}$C NMR signal of the carbene carbon. In the case of complex 16, the weak, almost indistinguishable signal, is the result of broadening and baseline saturation caused by a relatively labile silver-carbene bond. To establish the structure of 16 in solution, gradient heteronuclear multiple bond coherence (gHMBC) experiments were performed to elucidate C—H connectivities and confirm peak assignments. Long range coupling between the carbene carbon (182.9 ppm) of the imidazol-2-ylidene ring and the proximal methylene protons of the of the alkyne (4.38 ppm) N-substituent as well as the C4 and C5 protons of the imidazolium ring (6.92 and 7.36 ppm). The lack of a >200 ppm $^{13}$C-NMR chemical shift in conjunction with a detected resonance at 182.9 ppm, precludes the possibility of a free carbene and supports the assignment of a silver(I)-NHC complex.

Figure 11:
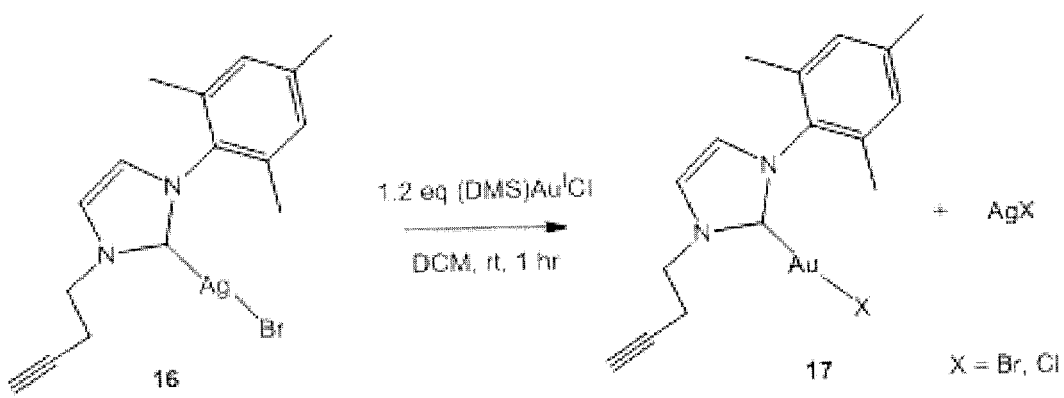
FIG. 11 shows a reaction scheme for the transmetalation of complex 16 to gold(I) complex 17.

Transmetalation of complex 16 to gold(I) proceeds rapidly upon treatment of the silver(I) species with 1.2 eq of chlorodimethylsulfide gold(I), as shown in FIG. 11. Solid AgCl immediately precipitates as the gold(I) ion coordinates and displaces silver(I) from the carbene carbon of the NHC ligand. Complete conversion of 16 to 17 requires only 15 minutes, as monitored by $^1$H and $^{13}$C-NMR spectroscopy. A diagnostic gold(I)-carbene $^{13}$C-NMR resonance of 172.0 ppm appears, along with new chemical shifts across the remainder of the spectrum.

Transmetalation proceeds rapidly and reaction times exceeding 1 h lead to the appearance of colloidal gold accompanied by a purple color change. Although this color change is indicative of complex decomposition or possible product conversion, no observable demetalation products (i.e., free ligand resonances) are observed spectroscopically; in fact, both the $^1$H and $^{13}$C-NMR spectra still indicate the presence of only one clean product in solution. An explanation for this phenomenon is that the decomposition products are comprised exclusively of NMR silent and/or chloroform insoluble species. To probe whether the appearance of colloidal gold forms as a consequence of a monocarbene to biscarbene conversion, or an oxidation state change from gold(I) to gold(III), a succinct NMR study was performed. The reaction of FIG. 11 was repeated on an NMR scale with 30 mg of 16. $^1$H and $^{13}$C NMR spectra obtained at variable time intervals indicate the initial transmetalation from silver (I) to gold(I) occurs with a clear $^{13}$C-NMR signal shift from ~184 to 172 ppm. The data support immediate formation of a single species that does not undergo subsequent mono- to bis-NHC conversion or metal ion oxidation processes.

Synthesis of Compound 10

1-Mesityl-3-(2-benzyleacetyl) imidazolium chloride 10 was prepared by adding compound 1' (0.640 g, 3.44 mmol), a magnetic stir bar, and 4 mL of dry toluene to a 250 mL round bottom flask. The mixture was allowed to stir for 2 min, whereupon benzyl chloroacetate 2'b (0.53 mL, 3.44 mmol) was added dropwise. The system was placed under Ar and heated to 110° C. for 6 h while stirring. The mixture was then allowed to cool and left to stir for an additional 12 h at room temperature. The solvent was removed in vacuo and the resulting colorless solid was triturated with ether (1.02 g, 79.9%). $^1$H-NMR (CDCl$_3$, 300 MHz) δ=10.41 (s, 1H), 7.94 (m, 1H), 7.34-7.32 (5H, m), 7.08 (m, 1H), 6.95 (s, 2H), 5.98 (s, 2H), 5.18 (s, 2H), 2.32 (s, 3H), 2.01, (s, 6H). $^{13}$C-NMR (CDCl$_3$, 125 MHz). δ=166.4 (C=O), 141.3, 139.7 (NCN), 139.7, 134.30, 134.3, 130.6, 129.7, 128.7, 128.6, 124.4, 122.3, 68.38, 50.57, 21.04, 17.39.

Synthesis of Compound 12

1-Mesityl-3-(2-benzyleacetyl)imidazolium gold(I) chloride 12 was prepared via an in situ transmetalation reaction. 0.201 g of 10 and 0.150 g of Ag$_2$O were suspended in 5 mL of dichloromethane and allowed to stir for 24 h in the dark. The resulting suspension was passed through a celite pad and fine frit filter directly into a stirring suspension of 0.075 g of (CH$_3$)$_2$SAu(I)Cl in 5 mL of dicholoromethane. The reaction mixture was allowed to stir at room temperature for 3.5 h in the dark. The mixture was then passed through a celite pad and medium frit to yield an amber colored filtrate. The solvent was concentrated and then treated with an excess of pentanes to precipitate a fine off-white powder. $^1$H-NMR (CDCl$_3$, 300 MHz) δ=7.38 (m, 5H), 7.23 (d, J=1.32 Hz, 1H), 6.95 (s, 2H), 6.92 (d, J=1.32 Hz, 1H), 5.24 (s, 2H), 5.14 (s, 2H), 2.32 (s, 3H), 1.99, (s, 6H). ESI-MS (positive ion, calculated for M=C$_{21}$H$_{22}$N$_2$O$_2$AuCl). 1155.1945 m/z [2M+Na]$^+$, 1097.2374 m/z [2M−Cl]$^+$, 589.0926 m/z [M+Na]$^+$, 531.1339 m/z [M−Cl]$^+$.

Hydrogenolysis Reaction

Compound 12 (30 mg) was dissolved in a 1:1 mixture of methanol: ethyl acetate (10 mL). This mixture was added to a solution of 1:1 methanol: ethyl acetate (5 mL) containing 5 mg of Pd/C. The reaction mixture was left to stir at room temperature under a balloon of H$_2$ for 24 h. After the allotted time, the solution was passed through a celite pad and fine frit. The solvent was removed in vacuo and a $^1$H-NMR of the residue was obtained (CDCl$_3$, 300 MHz) and indicated the presence of only starting material 12.

Synthesis of Compound 13

1-Mesityl-3-(1-butyne)imidazolium bromide 13 was prepared by dissolving 1.11 g (5.95 mmol) of 1-mesitylimidazole in 10 mL of toluene in a 100 mL round bottom flask. To this stirring solution, 0.84 mL (8.92 mmol) of cold 4-bromo-1-butyne was added dropwise. The reaction mixture was then placed under an ice water cooled condenser, heated to 120° C., and allowed to stir at this temperature for 3 d. After the reaction was complete an off-white residue formed a film on the inside of the reaction vessel. 20 mL of diethyl ether was added directly to the reaction mixture and the contents were stirred vigorously for 3 h at room temperature. The suspension was filtered and the solid was collected on a Buchner funnel and washed with 3×10 mL of diethyl ether. The resulting off-white solid was then dried under vacuum for 24 h (0.70 g, 63.4%). Heteronuclear multiple bond coherence (gHMBC) was applied to determine C—H connectivities and confirm peak assignments. $^1$H-NMR (CDCl$_3$, 500 MHz) δ=10.15 (s, 1H), 8.23 (s, 1H), 7.17 (s, 1H), 6.97 (s, 2H), 4.89 (t, J=5.85 Hz, 2H), 2.99 (dt, J=5.85 Hz, J=1.95 Hz, 2H), 2.31 (s, 3H), 2.05 (s, 6H), 2.05 (t, J=1.95 Hz, 1H). $^{13}$C-NMR (CDCl$_3$, 125 MHz): δ=141.3, 137.9 (NCN), 134.2, 130.6, 129.8, 123.9, 122.7, 79.06, 72.54, 48.56, 21.07, 21.04, 17.56. ESI-MS (positive ion, calculated for M=C$_{16}$H$_{19}$BrN$_2$). 355.0402 m/z [M+Cl]$^+$, 319.0802 m/z [M+H]$^+$, 239.1554 m/z [M−Br]$^+$.

Synthesis of Compound 14

1-Benzyl-3-(1-butyne)imidazolium bromide 14 was prepared by a similar synthetic procedure as 13 using 1.00 g (6.32 mmol) of 1-benzyl-imidazole, 0.71 mL (7.59 mmol) of 4-bromo-1-butyne, and 15 mL of toluene. The resulting off-white powder was collected on a Buchner funnel and dried under vacuum for 24 h (1.48 g, 80.2%). Heteronuclear multiple bond coherence (gHMBC) was applied to determine C—H connectivities and confirm peak assignments. $^1$H-NMR (CDCl$_3$, 500 MHz) δ=10.45 (s, 1H), 7.75 (s, 1H), 7.45 (d, J=1.6 Hz, 2H), 7.42 (s, 1H), 7.34 (d, J=1.6 Hz, 2H), 7.33 (d, J=1.6 Hz, 1H), 5.57 (s, 2H), 4.51 (t, J=6.3 Hz, 2H), 2.84 (dt, J=6.3 Hz, J=2.6 Hz, 2H), 2.08 (t, J=2.6 Hz, 1H). $^{13}$C-NMR (CDCl$_3$, 125 MHz): δ=137.1 (NCN), 132.8, 129.5, 129.4, 128.9, 122.8, 121.6, 78.69, 72.90, 53.35, 48.42, 20.79. ESI-MS (positive ion, calculated for M=C$_{14}$H$_{15}$BrN$_2$). 327.0070 m/z [M+Cl]$^+$, 291.0484 m/z [M+H]$^+$, 211.1238 m/z [M+Br]$^+$.

Synthesis of Compound 15

1-tert-Butyl-3-(1-butyne)imidazolium bromide 15 was prepared by a similar synthetic procedure as 13 but with a slightly modified work-up. The synthesis was performed using 1.11 mL (8.05 mmol) of 1-(tert-butyl)-imidazole, 1.13 mL (12.1 mmol) of 4-bromo-1-butyne, and 10 mL of toluene. After the reaction was complete, the mixture was allowed to cool to room temperature and 20 mL of diethyl ether was added directly to the reaction vessel. The mixture was stirred for 10 min and the supernatant was decanted. The off-white residue was resuspended in 10 mL of fresh diethyl ether, stirred for 10 min and the supernatant was decanted (this was repeated 2 more times). After the final decanting, the solid was suspended in 2 mL of diethyl ether, transferred directly to a vial. The remaining solvent was removed in vacuo and the resulting off-white, very hygroscopic solid was dried under vacuum for 24 h before transferring to an Ar filled glovebox for storage (0.453 g, 21.9%). $^1$H-NMR (CDCl$_3$, 300 MHz) δ=10.47 (s, 1H), 7.75 (s, 1H), 7.55 (s, 1H), 4.62 (t, J=6.3 Hz, 2H), 2.88 (dt, J=6.3 Hz, J=2.2 Hz, 2H), 2.07 (t, J=2.2 Hz, 1H), 1.68 (s, 9H). $^{13}$C-NMR (CDCl$_3$, 125 MHz): δ=135.7 (NCN), 123.0, 119.2, 79.07, 72.38, 60.38, 48.04, 29.99, 20.77.

Synthesis of Compound 16

1-Mesityl-3-(1-butyne)imidazol-2-ylidene silver(I) bromide 16 was prepared by deprotonation and direct metalation with silver(I) oxide. Inside an Ar filled glovebox, 303.0 mg (0.949 mmol) of compound 13 was added to a vial and dissolved in 4 mL of chloroform. 151.1 mg (0.652 mmol) of silver(I) oxide was added directly as a solid to this stirring solution. The reaction vessel was wrapped in aluminum foil and allowed to stir for 3 d at room temperature. The reaction mixture was passed through a pad of celite atop a filter paper fitted glass pipette to remove any insoluble gray particulates. The amber colored filtrate was reduced in vacuo to 1 mL whereupon an excess of diethyl ether (~5 mL) was added to precipitate an off-white solid. The supernatant was decanted, the solid was resuspended in 2 mL of diethyl ether, and the supernatant was decanted again (this was repeated 2 more times with 2×2 mL of diethyl ether). The solid was dried completely under vacuum to give an off-white solid (264.5 mg, 65.4%). Heteronuclear multiple bond coherence (gHMBC) was applied to determine C—H connectivities and confirm peak assignments. $^1$H-NMR (CDCl$_3$, 500 MHz) δ=7.36 s, 1H), 6.94 (s, 2H), 6.92 (s, 1H), 4.38 (t, J=6.3 Hz, 2H), 2.76 (dt, J=6.3 Hz, J=1.7 Hz, 2H), 2.33 (s, 3H), 2.04 (t, J=1.7 Hz, 1H), 1.94 (s, 6H). $^{13}$C-NMR (CDCl$_3$, 125 MHz): δ=182.9 (C$_{carbene}$), 139.5, 135.4, 134.7, 129.4, 122.5, 121.4, 79.72, 72.17, 50.16, 21.87, 21.06, 17.63.

Synthesis of Compound 17

1-Mesityl-3-(1-butyne)imidazol-2-ylidene gold(I) halide 17 was prepared by a transmetalation reaction from compound 16. The following steps were performed inside an Ar filled glovebox and taking care to minimize light exposure. 152.3 mg (0.357 mmol) of compound 16 was dissolved in 4 mL of chloroform. To this stirring mixture, 126.3 mg (0.429 mmol) of chlorodimethylsulfide gold(I) was added directly as a solid over the course of 2 min whereupon a white solid immediately precipitated. The reaction vessel was capped and left to stir in the dark at room temperature for 1 h. The cloudy grayish purple reaction mixture was passed through a celite pad atop a filter paper fitted glass pipette in an attempt to remove the colloidal gold. The filtrate was reduced to 1 mL under vacuum and an excess of diethyl ether was added to precipitate a bright white solid. The supernatant was decanted and the solid was resuspended in diethyl ether (3 mL). This was repeated two more times (2×3 mL diethyl ether). An accurate yield could not be obtained due to intractable colloidal gold. Heteronuclear multiple bond coherence (gHMBC) was applied to determine C—H connectivities and confirm peak assignments. $^1$H-NMR (CDCl$_3$, 500 MHz) δ=7.31 (d, J=1.39 Hz, 1H), 6.94 (s, 2H), 6.86 (d, J=1.39 Hz, 1H), 4.41 (t, J=6.35 Hz, 2H), 2.84 (dt, J=6.35 Hz, J=2.58 Hz, 2H), 2.31 (s, 3H), 2.07 (t, J=2.58 Hz, 1H), 2.00 (s, 6H). $^{13}$C-NMR (CDCl$_3$, 125 MHz): δ=172.0 (C$_{carbene}$), 139.7, 134.7, 134.7, 129.4, 121.8, 121.3, 79.52, 72.02, 49.68, 21.40, 21.08, 17.73.

Synthesis of 19

Inside an Ar filled glovebox, solid ligand 18 (260 mg, 0.6 mmol, 1 equiv.) and Ag$_2$O (97.32 mg, 0.4 mmol, 0.7 equiv.) were dissolved in dichloromethane (10 mL) and stirred for 2 days to provide the NHC—Ag complex 19 in situ. To the reaction mixture was added (CH$_3$)$_2$SAuCl (176.73 mg, 0.6 mmol, 1 equiv.) and stirred for 1 h. Then the reaction mixture was filtered through Celite®. The filtrate was collected and reduced under vacuum to 1 ml. Diethyl ether was added to precipitate a pale yellow powder. The solid was collected by filtration and dried under vacuum for 2 h to provide the NHC—Au complex 19 (112.5 mg, Yield=45%). $^1$H NMR (300 MHz, CDCl3): δ=8.18 (s, 2H, HAr), 7.29-7.53 (m, 6H, HAr), 5.84 (s, 2H, N—CH$_2$), 4.13 (s, 3H, N—CH$_3$) ppm. $^{13}$C NMR (CDCl$_3$, 500 MHz): δ=179.6 (NCN), 161.9 (COO), 141.5 (C—Ar), 136.1 (C—F), 134.4 (C—F), 134.1 (C—Ar), 132.7 (C—F), 132.7 (C—Ar), 131.5 (C—Ar), 127.2 (C—Ar), 125.1 (C—Ar), 125.0 (C—Ar), 119.9 (C—Ar), 116.6 (C—Ar), 111.7 (C—Ar), 52.3 (N—C—Ar), 35.4 (N—CH$_3$) ppm. $^{19}$F NMR (CDCl$_3$, 235 MHz): δ=−152.77 (t, $^3J_{F,F}$=19.1 Hz, 2 F, ArF), −158.05 (t, $^3J_{F,F}$=23.2 Hz, 1 F, ArF), −162.55 (dd, $^3J_{F,F}$=19.1, 23.2 Hz, 2 F, ArF) ppm. Anal. Calcd for C$_{22}$H$_{13}$AuClF$_5$N$_2$O$_2$ (664.03 g mol$^{-1}$): C: 39.75%; H: 1.97%; N: 4.21%, Found: C: 39.89%; H: 2.10% N: 4.42%.

Synthesis of aptamer-drug conjugate 1-(methyl)-3-(4-N-sgc8c-aptamer-carbamoylbenzyl)benzo[d]imidazolium gold(I) chloride 21

In a 2 ml synthesis tube, complex 19 (6 mg, 9 μmol) was dissolved in 1 ml THF, and triethylamine (1 mg, 9 μmol) was added drop wise. After 10 min of shaking, 1 ml aqueous solution of aptamer 20 (0.1 μmol) was added to the tube, and the mixture was shaken for 24 h. Then the reaction mixture was separated and purified by HPLC and gel electrophoresis.

Synthesis of 1-(anthracen-9-ylmethyl)-1H-benzo[d]imidazole (24)

The mixture of benzimidazole 22 (354 mg, 3 mmol), tetrabutylammonium bromide (TBAB) (96 mg, 0.3 mmol), THF (10 mL) and 50% aqueous K2CO3 (10 mL) was stirred. 9-(chloromethyl)anthracene 23 (678 mg, 3 mmol) was added in portions. Then, the mixture was heated to 70° C. for 40 h. After heating the mixture was cooled to room temperature and extracted by dichloromethane (DCM). The organic layer was dried with NaSO$_4$. The solvent was removed in vacuo to give compound 24 as a yellow solid. (700 mg, Yield=76%). $^1$H NMR (300 MHz, CDCl3): δ=8.63

(s, 1H, N—CH—N), 8.10 (s, 4H, HAr), 7.82-7.37 (m, 9H, HAr), 6.21 (s, 2H, N—CH$_2$). $^{13}$C NMR (CDCl$_3$, 500 MHz): δ=143.93 (NCN), 142.14 (C—Ar), 134.18 (C—Ar), 131.40 (C—Ar), 129.69 (C—Ar), 129.48 (C—Ar), 127.52 (C—Ar), 125.38 (C—Ar), 122.92 (C—Ar), 122.41 (C—Ar), 120.50 (C—Ar), 109.49 (C—Ar), 41.34 (N—CH$_2$) ppm.

Synthesis of 26

To a solution of 24 (500 mg, 1.6 mmol) in dry THF (10 mL) was added dropwise a solution of 25 (610 mg, 1.6 mmol) in THF (10 mL). After complete addition, the mixture was refluxed for 48 h during which time a yellow precipitate formed. The solvent was decanted from the precipitate and the solid was washed with THF (3×10 mL) and then dried in vacuo to give a yellow solid 26 (504 mg, 51% yield). $^1$H NMR (300 MHz, CDCl3): δ=12.03 (s, 1H, N—CH—N), 8.57-8.64 (m, 3H, HAr), 8.15 (m, 4H, HAr), 7.67-7.41 (m, 9H, HAr), 7.13 (m, 1H, HAr), 6.89 (s, 2H, CH$_2$-anthracene), 6.07 (s, 2H, CH$_2$—Ar) ppm. $^{19}$F NMR (CDCl$_3$, 300 MHz): δ=−152.38 (t, $^3J_{F,F}$=19.1 Hz, 2 F, ArF), −157.53 (t, $^3J_{F,F}$=23.2 Hz, 1 F, ArF), −162.09 (dd, $^3J_{F,F}$=19.1, 23.2 Hz, 2 F, ArF) ppm.

DART-MS (positive ion, calculated for M=C$_{36}$H$_{22}$BrF$_5$N$_2$O$_2$). 609.1612 m/z [M+H]+.

Synthesis of 1-(anthracen-9-ylmethyl)-3-(4-N-sgc8c-aptamer-carbamoylbenzyl) benzo[d]imidazolium gold(I) chloride 27

Inside an Ar filled glovebox, solid ligand 26 (100 mg, 0.16 mmol, 1 equiv.) and Ag$_2$O (26 mg, 0.11 mmol, 0.7 equiv.) were dissolved in DCM (5 mL) and stirred for 2 days to provide the NHC—Ag complex in situ. To the reaction mixture was added (CH$_3$)$_2$SAuCl (50 mg, 0.16 mmol, 1 equiv.) and stirred for 1 h. Then, the reaction mixture was filtered through Celite®. The filtrate was collected and reduced under vacuum to 0.5 ml. Diethyl ether was added to precipitate a pale yellow powder. The solid was collected by filtration and dried under vacuum for 2 h to provide the NHC—Au complex 27 (98 mg, Yield=71%). $^1$H NMR (300 MHz, CDCl3): δ=8.63-8.53 (m, 3H, HAr), 8.13 (m, 4H, HAr), 7.63-7.49 (m, 6H, HAr), 7.15 (m, 2H, HAr), 6.84 (s, 2H, N—CH$_2$-anthracene), 5.92 (s, 2H, N—CH$_2$—Ar) ppm. $^{13}$C NMR (CDCl$_3$, 500 MHz): δ=180.55 (NCN), 161.9 (COO), 141.5 (C—Ar), 136.1 (C—F), 134.4 (C—F), 134.1 (C—Ar), 132.7 (C—F), 132.7 (C—Au), 161.87 (COO), 141.54 (C—Ar), 133.44 (C—Ar), 131.42 (C—Ar), 129.87 (C—Ar), 127.64 (C—Ar), 127.37 (C—Ar), 125.35 (C—Ar), 124.64 (C—Ar), 123.20 (C—Ar), 122.03 (C—Ar), 112.98 (C—Ar), 111.46 (C—Ar), 52.36 (N—C-Antracene), 47.90 (N—CH$_2$—Ar) ppm. 19F NMR (CDCl$_3$, 235 MHz): δ=−152.32 (t, $^3J_{F,F}$=19.1 Hz, 2 F, ArF), −157.66 (t, $^3J_{F,F}$=23.2 Hz, 1 F, ArF), −162.15 (dd, $^3J_{F,F}$=19.1, 23.2 Hz, 2 F, ArF) ppm. DART-MS (positive ion, calculated for M=C$_{36}$H$_{22}$AuClF$_5$N$_2$O$_2$). 858.1236 m/z [M+NH$_4$]+.

Synthesis of 1-(anthracen-9-ylmethyl)-3-(4-N-sgc8c-aptamer-carbamoylbenzyl) benzo[d]imidazolium triphenylphosphino gold(I) tetrafluoroborate 31

Figure 21:
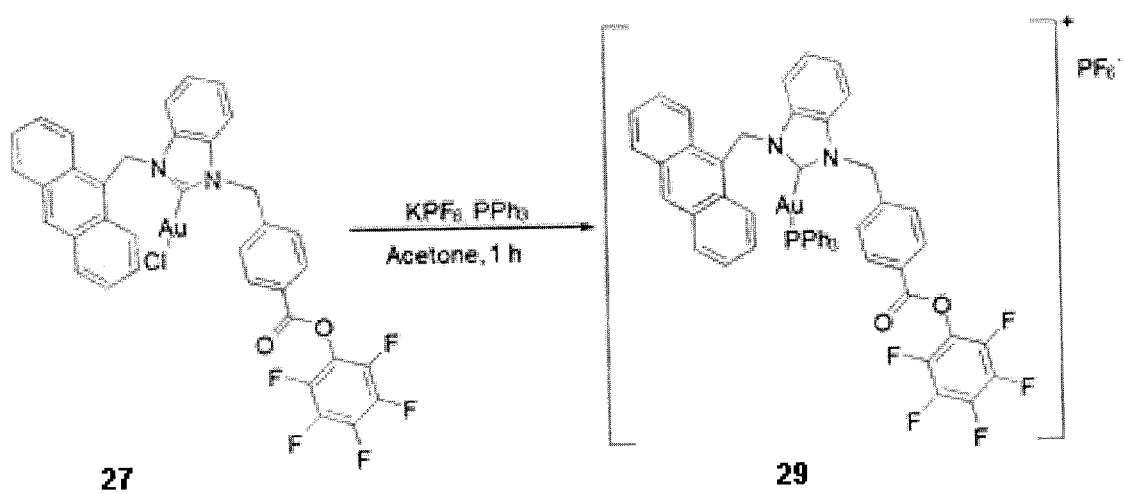
FIG. 21 is a reaction scheme for the preparation of 29, a fluorescent drug bound NHC-gold complex for conjugation with an amine functionalized aptamer, from 27 according to an embodiment of the invention.

As indicated in FIG. 21, a 100 mg portion of complex 27 was dissolved in 5 ml of acetone, then 35 mg of triphenylphophine (0.133 mmol, 1.1 equiv.) and 24 mg of KPF$_6$ (0.133 mmol, 1.1 equiv.) were added. The mixture was stirred at room temperature for 1 hour. After which, the mixture was filtered through Celite and the filtrate was dried under vacuum. The yellow residue was dissolved in 2 ml of DCM and washed several times with water, then 10 ml of hexane was added to the organic solution to precipitate the cationic NHC—Au complex 29. Complex 29 was purified by washing with hexane for 3 times (0.112 g, yield=81.7%). %). $^1$H NMR (300 MHz, CDCl$_3$): δ=8.21 (d, 2H, HAr), 8.05 (s, 1H, HAr), 7.94 (d, 2H, HAr), 7.79 (m, 3H, HAr), 7.55 (m, 9H, HAr), 7.41 (m, 10H, HAr), 7.16 (d, 2H, HCAr), 6.56 (s, 2H, CH$_2$-antrancene), 5.86 (s, 2H, CH$_2$-benzyl) ppm. $^{13}$C{$^1$H} NMR (CDCl$_3$, 125 MHz): δ=194.01 (C—Au), 193.03 (C—Au), 162.00 (C=O), 142.56 (C—Ar), 138.49 (C—Ar), 138.03 (C—Ar), 134.11 (C—Ar), 131.39 (C—Ar), 129.40 (C—Ar), 127.56 (C—Ar), 125.42 (C—Ar), 123.05 (C—Ar), 112.27 (C—Ar), 52.12 (CH$_2$-antrancene), 42.09 (CH$_2$-benzyl) ppm. $^{31}$P NMR (CDCl$_3$, 121 MHz): δ=106.10 (q, PF$_6$), 38.34 (s, Au—PPh$_3$) ppm. DART-MS (positive ion, for M+=C$_{54}$H$_{36}$AuF$_5$N$_2$O$_2$P). [M]$^+$ calcd for 1067.2095; Found: 1067.2101.

Synthesis and Biology Assay of Aptamer-Drug Conjugates

Figure 12:
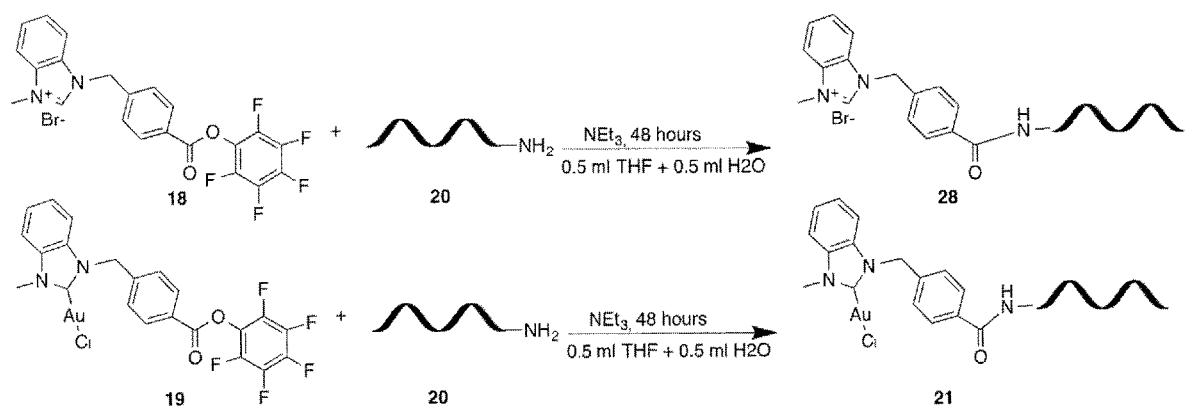
FIG. 12 shows a reaction scheme for the generation of a ligand conjugate 28 and an NHC-gold conjugate 21, according to an embodiment of the invention.

A NH$_2$-modified sgc8c aptamer was synthesized and purified based on that reported in Shangguan et al. Clin. Chem. 2007, 53(6), 1153-5. As shown in FIG. 12, aptamer 20 was treated with 100 equivalent of the NHC—Au complex 19 and 100 equivalent trimethylamine in THF/Water (1/1) at room temperature. After two days, the reaction mixture was purified by gel electrophoresis and HPLC. The conjugation reaction between the ligand 18 and sgc8c aptamer 20 was conducted under the same conditions to give conjugate 28.

Synthesis of an Anthracene Dye-Tagged NHC—Au Complexes

Figure 14:
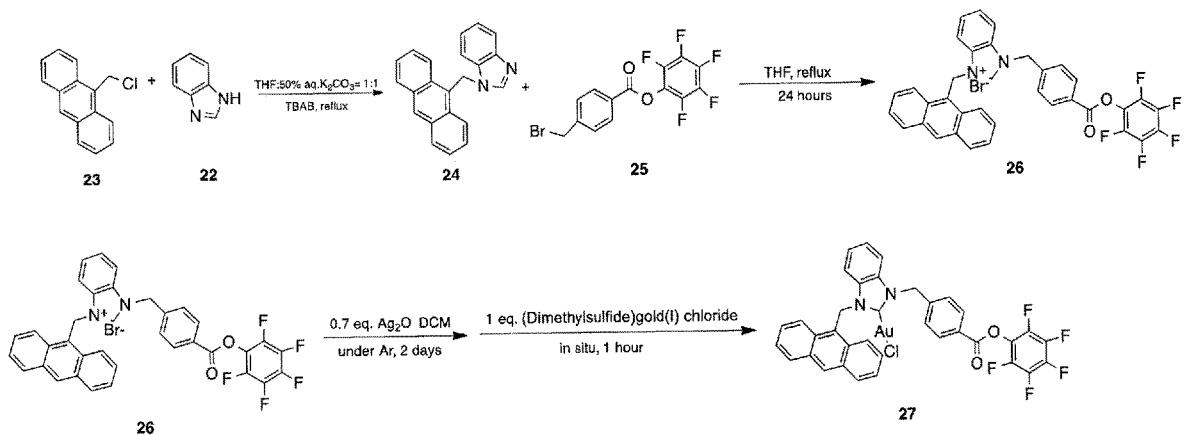
FIG. 14 is a reaction scheme for the preparation of 27, a fluorescent drug bound NHC-gold complex for conjugation with an amine functionalized aptamer, according to an embodiment of the invention.

As a tool for monitoring the uptake of the metal-aptamer conjugate and for confirming successful conjugation to the aptamer, a dye was tagged to the Au complex, as indicated in FIG. 14

Figure 15:
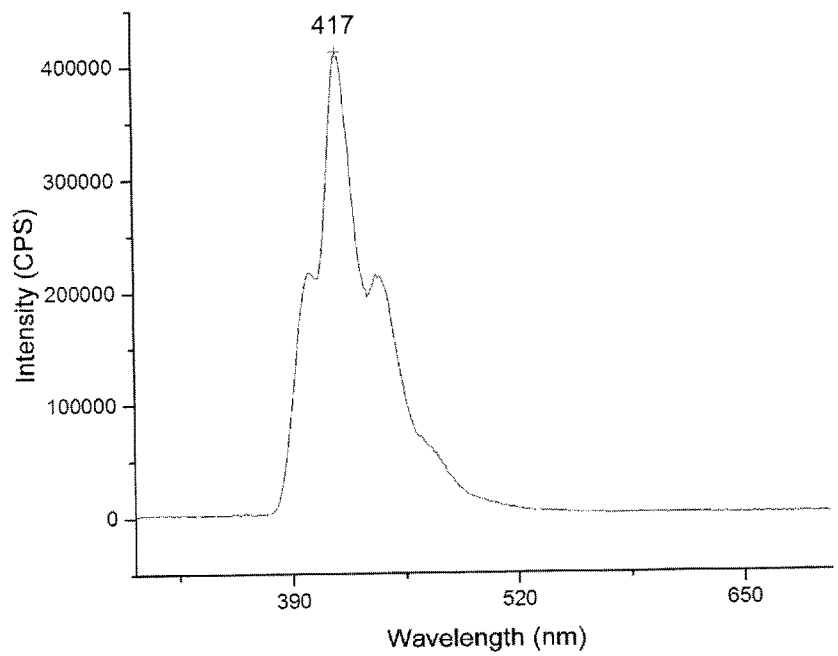
FIG. 15 is an emission spectrum of compound 27 under excitation at 389 nm.

As shown in FIG. 14, 9-(chloromethyl)anthracene 23 and benzimidazole 22 were stirred in THF and aqueous K$_2$CO$_3$ solution (1:1) for 2 days, forming the yellow-brown solid 24. Then compound 25 was added to produce ligand precursor 26 as a yellow solid. The metallation reaction gave compound 27 as a yellow powder. Compound 27 has a blue fluorescence under 365 nm UV light. The luminescent spectrum of the NHC-Gold compound 27 was measured by dissolving 1 mg of 27 in 1 ml acetonitrile, as shown in FIG. 15.

Synthesis of a Fluorescein Dye-Tagged Aptamer

Figure 16:
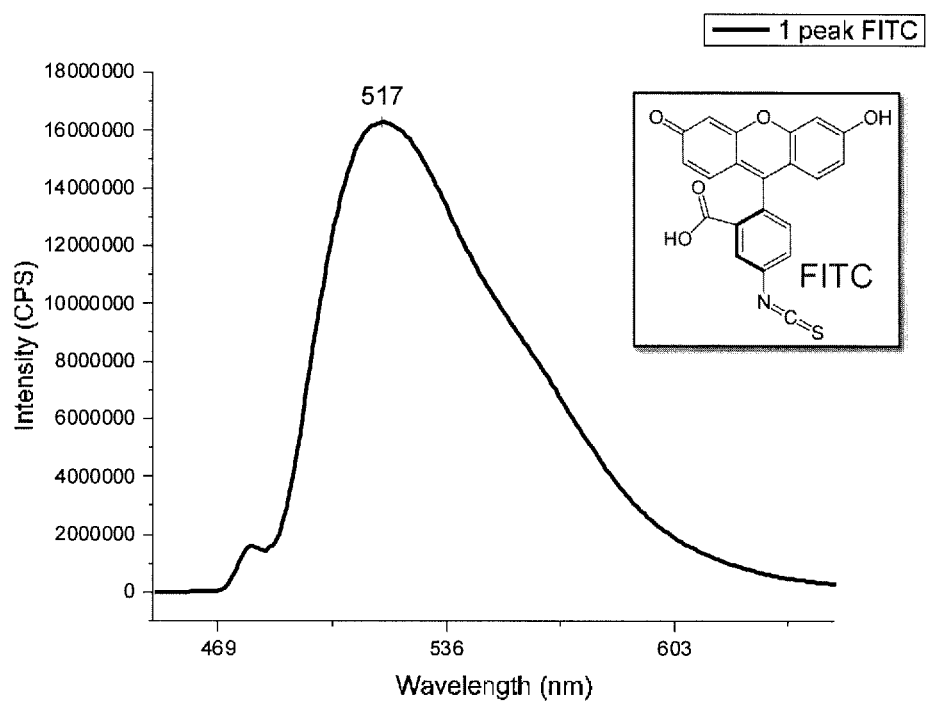
FIG. 16 is an emission spectra of FITC in water under excitation at 389 nm.

The coupling of fluorescein isothiocyanate (FITC) to NH$_2$-modified sgc8c aptamer was carried out. The FITC-sgc8c aptamer exhibits yellow-green fluorescence under 365 nm UV light, as does FITC shown in FIG. 16.

Synthesis of Aptamer-Dye-Drug NHC—Au Conjugate

Figure 17:
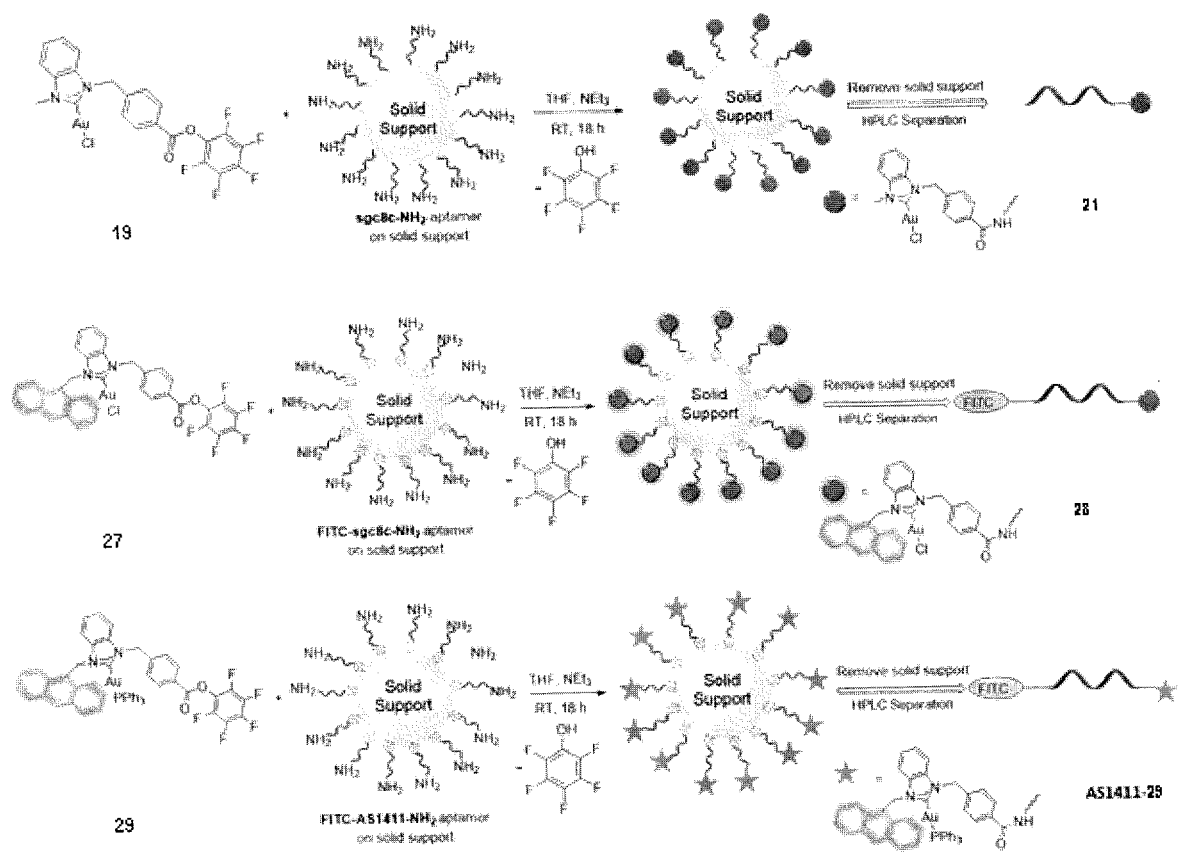
FIG. 17 is a reaction scheme for conjugation of a fluorescent dye bound NHC-gold complex with an amine functionalized sgc8-aptamer or AS1411, according to an embodiment of the invention.

FITC-sgc8c aptamer on the solid support bead were treated with 100 equivalent of triethylamine and 100 equivalent of compound 27 in THF as indicated in FIG. 17. The reaction was carried out for 18 h at room temperature, after which excess 27 and triethylamine were washed from the solid support beads. The beads, which have the aptamer and reaction products attached thereto, were incubated with 2 ml ammonium hydroxide and methylamine solution (1:1) at 65° C. for 20 min to release the conjugate. The crude product was purified by high performance liquid chromatography.

Figure 18:
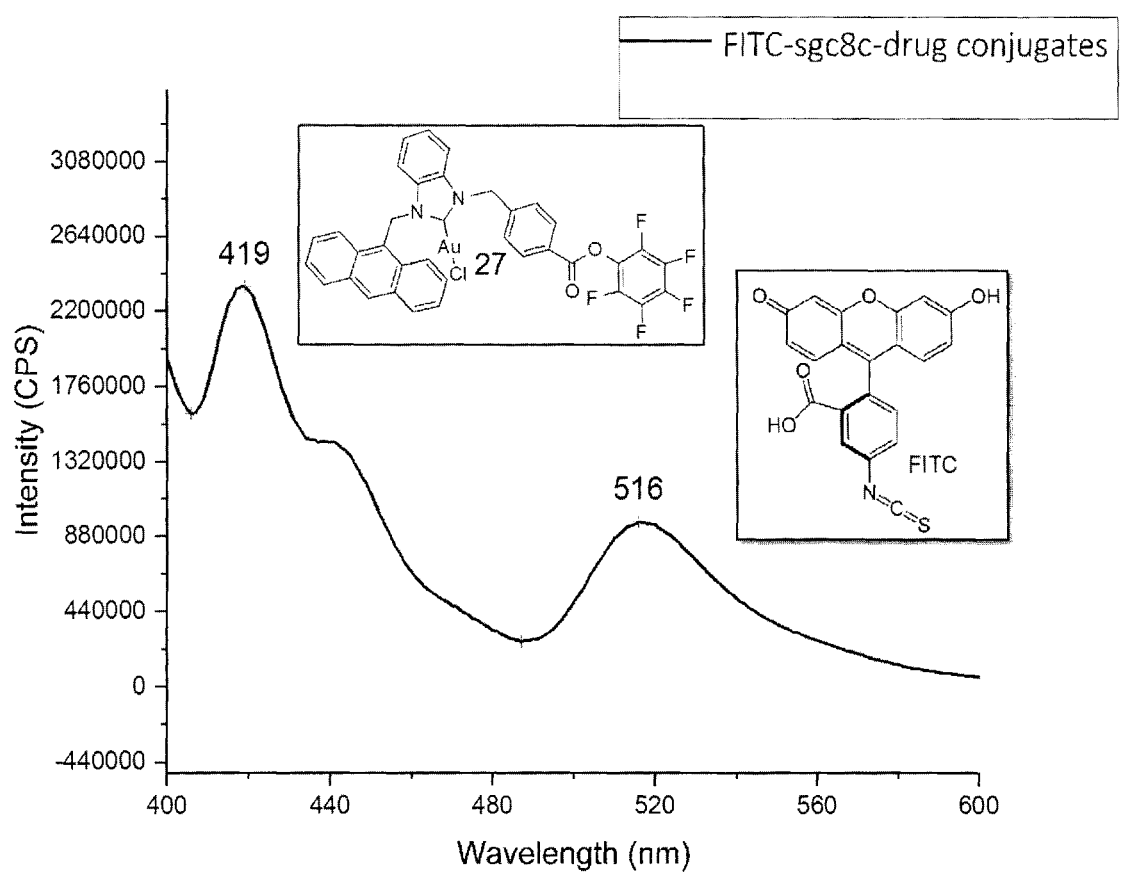
FIG. 18 is an emission spectra of the conjugate between fluorescent dye bound NHC-gold complex with an amine functionalized sgc8-aptamer, according to an embodiment of the invention as isolated by HPLC.

Pure FITC-sgc8c aptamer, has a retention time by HPLC of 16 min. After reaction, a concentrated component peak for the aptamer-dye-drug NHC—Au conjugate 30 (sgc8c-27) has a retention time of 24 min. This component was collected and dried. In the spectrum, shown in FIG. 18, emission peaks for FITC and the emission peak of 27 are observed.

Cell Viability Studies

Cell Culture:

Cell lines CEM (T cell leukiemia) and Ramos (Burkitt's Lymphoma) were cultured according to ATCC specifications in RPMI-1640 medium. The medium was supplemented with 10% fetal bovine serum (Invitrogen) and the cells were incubated at 37° C. in 5% $CO_2$.

Cytotoxicity Studies Using MTS Assay:

CEM and Ramos cells were treated at the following concentrations of compound 9 that were prepared by dilution of an aqueous solution of 20 mM 9: 0.5 µM, 1.0µ, 3.5µ, 5.0µ, 7.5µ, 10µ, 15µ, and 25 µM, respectively, for 48 h at 37° C. In addition to treatments, two negative controls, cells in media and water (0.01%) treated cells, were carried out. Approximately 30 µL of 10,000 freshly collected CEM cells were added to each well of a 96-well plate. Similarly, Ramos cells were added to a separate 96-well plate. Both plates were incubated at 37° C. in 5% $CO_2$ for 24 h before beginning experiments. After 24 h incubation, 30 µL of each concentration of 9 was added to eight wells of each of the 96-well plates and to a third plate with wells containing no cells (30 L of media for background measurements). Each of the three plates was subjected to treatment and incubated for 48 h at 37° C. in 5% $CO_2$. After 48 h, 30 µL of MTS dye, (3-(4,5-dimethylthiazol-2-yl)-5-(3-carboxymethoxyphenyl)-2-(4-sulfophenyl)-2H-tetrazolium), were added to each well. The assay was allotted 4 h at 37° C. for development. After incubation with the MTS dye, the 490 nm absorbance was read on a Tecan plate 110 reader for each well. Each cell measurement had the treatment background subtracted before analysis. Quantitative and statistical analyses were done using the Origin 8.5 software. The same procedures were used to study compound 27 to assess whether the proligand displayed any cytotoxicity.

Figure 13A:
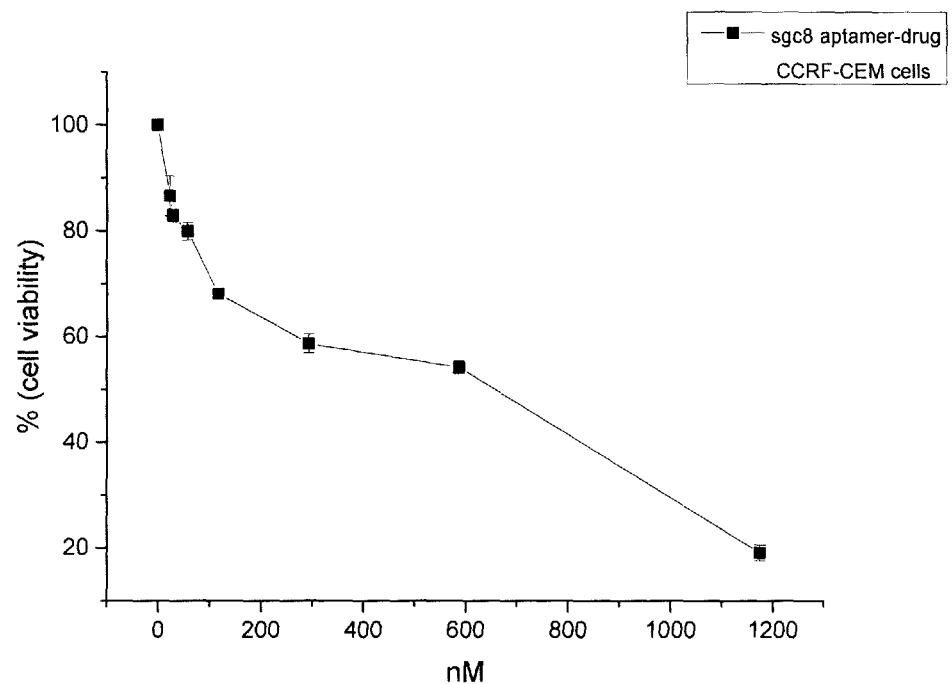
FIG. 13A is a plot of cell viability in the presence of 21 aptamer-NHC-gold conjugate and FIG. 13B in the presence of 28.
Figure 13B:
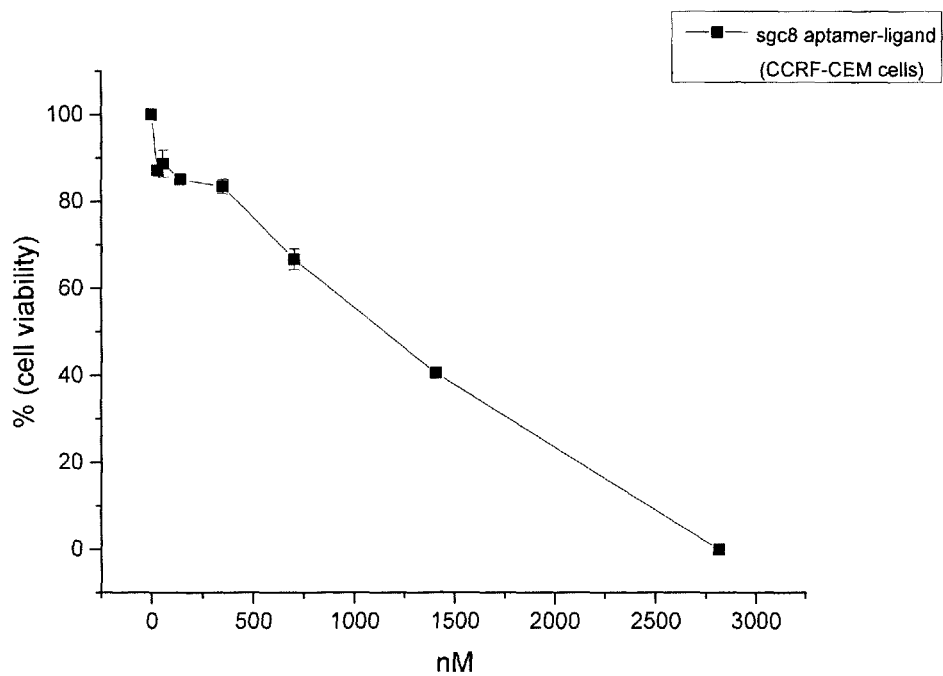
Figure 19A:
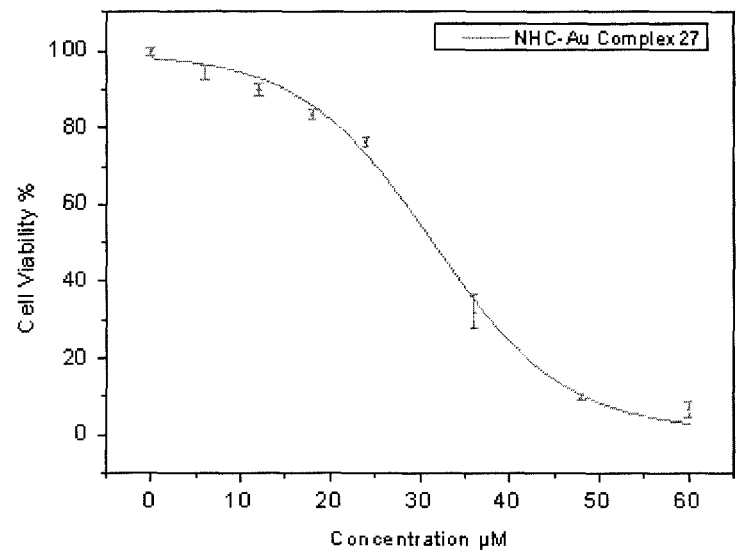
FIG. 19A shows a plot of MTS assays of complex 27 with CCRF-CEM cell line. $IC_{50}$=31.1±2.11 µM.
Figure 19B:
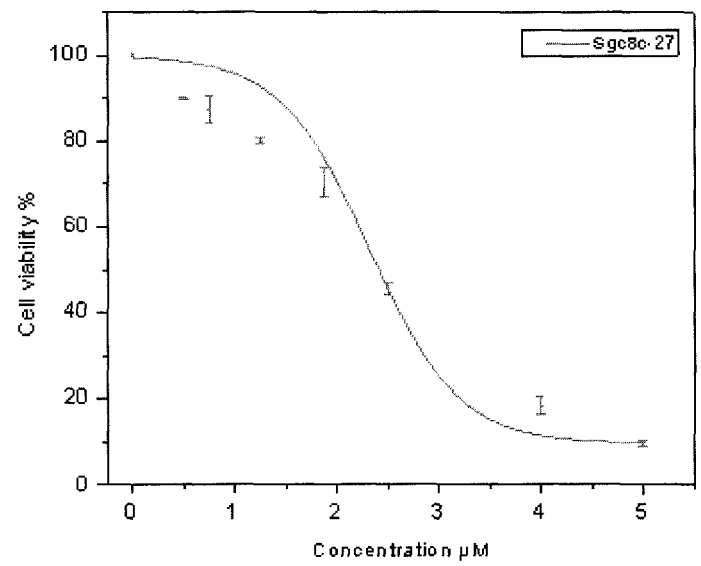
FIG. 19B shows a plot of MTS assays of conjugate 30 (sgc8c-27) with CCRF-CEM cell line. $IC_{50}$=2.39±1.50 µM.
Figure 19C:
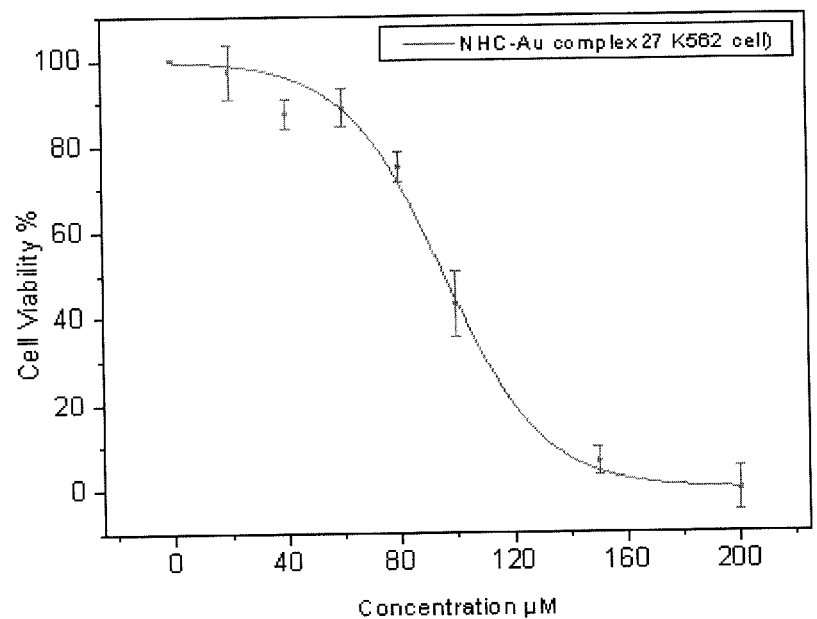
FIG. 19C shows a plot of MTS assays of complex 27 with K562 cell line.
Figure 20:
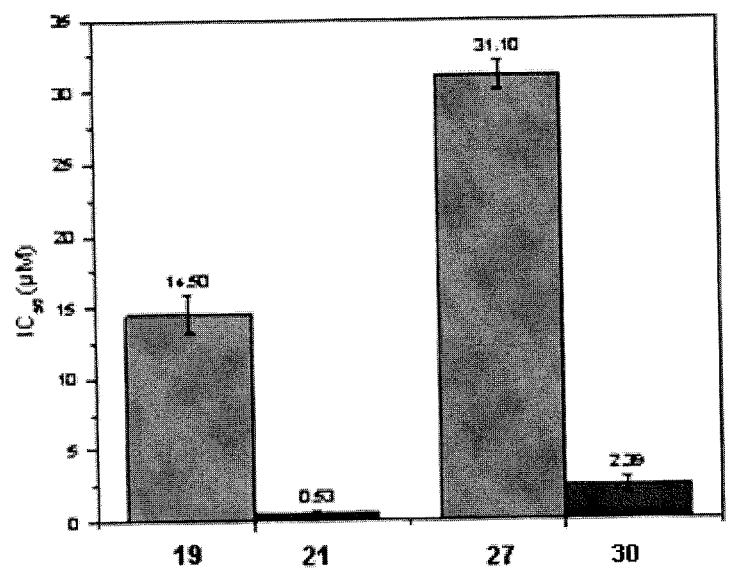
FIG. 20 shows a bar chart for comparison of the cytotoxicity between NHC—Au complexes 19 and 27 and their corresponding conjugates 21 (sgc8c-19) and 30 (sgc8c-27).
Figure 22:
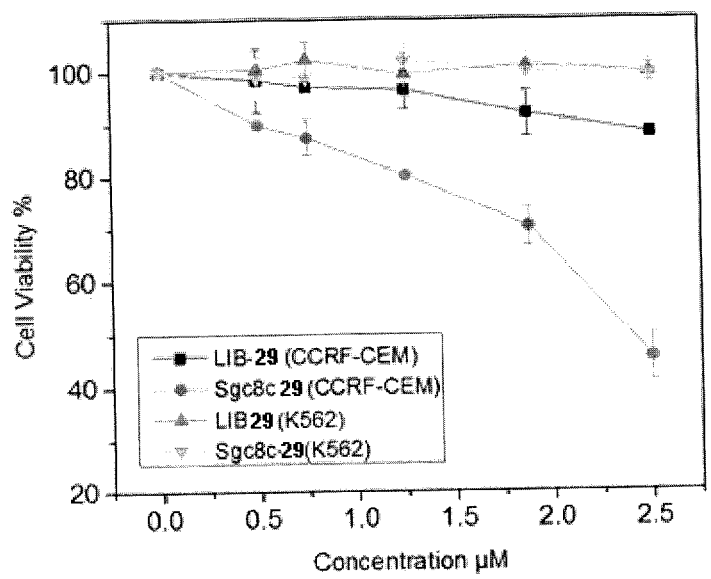
FIG. 22 shows a composite plot of MTS cell proliferation assays that demonstrate the specific cytotoxicity of complex 27 and its conjugate 30sgc8c-27, according to an embodiment of the invention, towards CCRF-CEM cells CCRF-CEM and K562 cells.
Figure 25A:
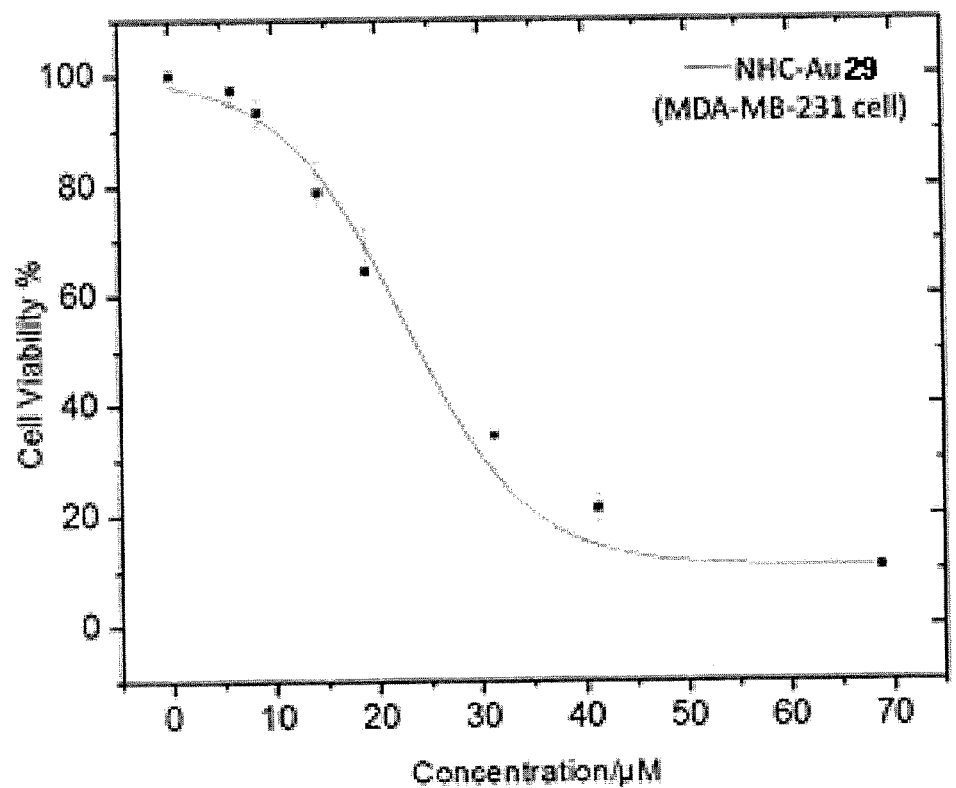
FIG. 25A is a plot of the cell viability vs concentration for the MTS assay of complex 29 with MDA-MB-231 cell line. $IC_{50}=21.1\pm1.06$ μM.
Figure 25B:
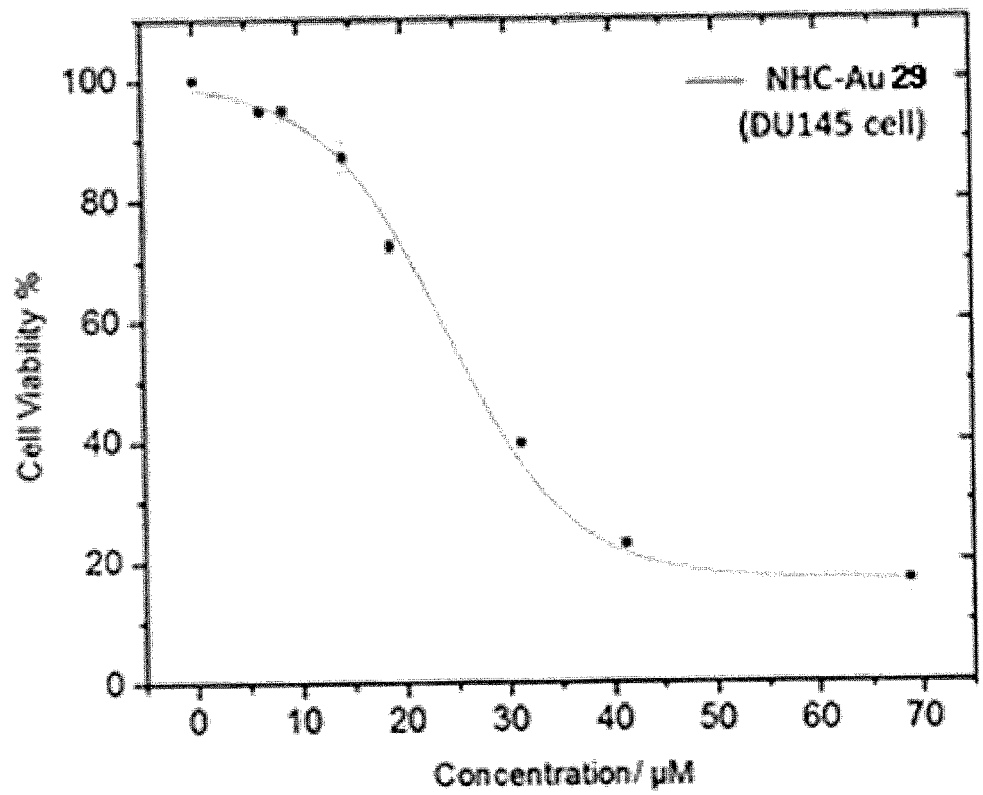
FIG. 25B is a plot of the cell viability vs concentration for the MTS assay of complex 29 with DU145 cell line. $IC_{50}=21.1\pm1.06$ μM.
Figure 25C:
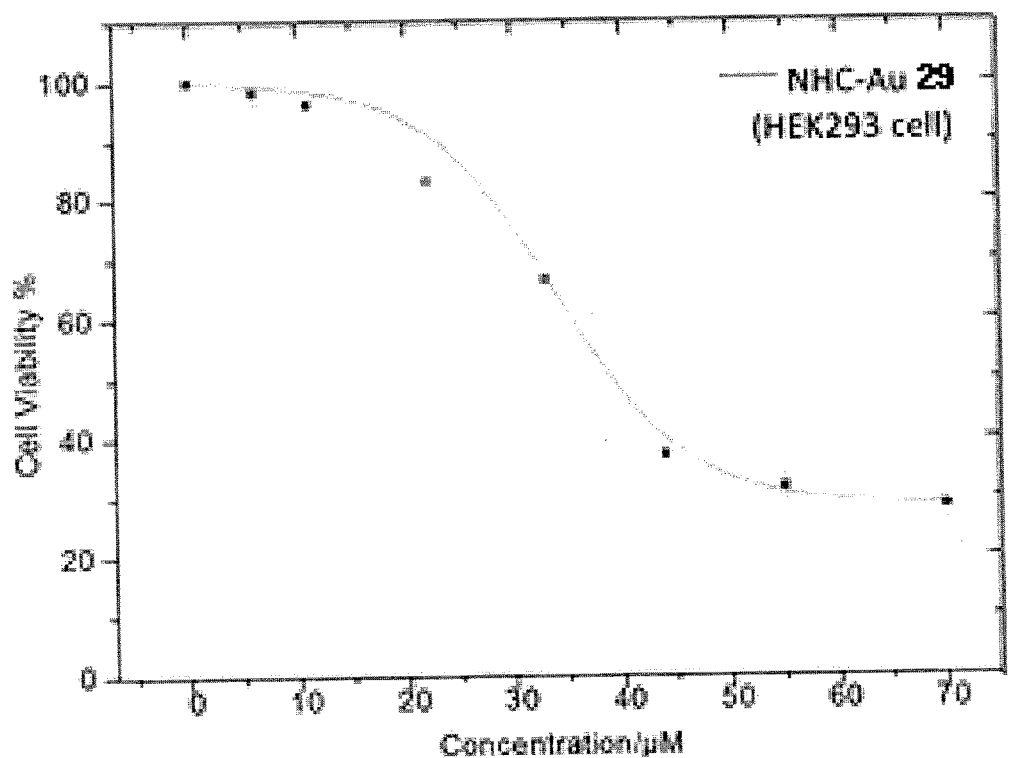
FIG. 25C is a plot of the cell viability vs concentration for the MTS assay of complex 29 with HEK293 cell line. $IC_{50}=38.7\pm1.18$ μM.
Figure 25D:
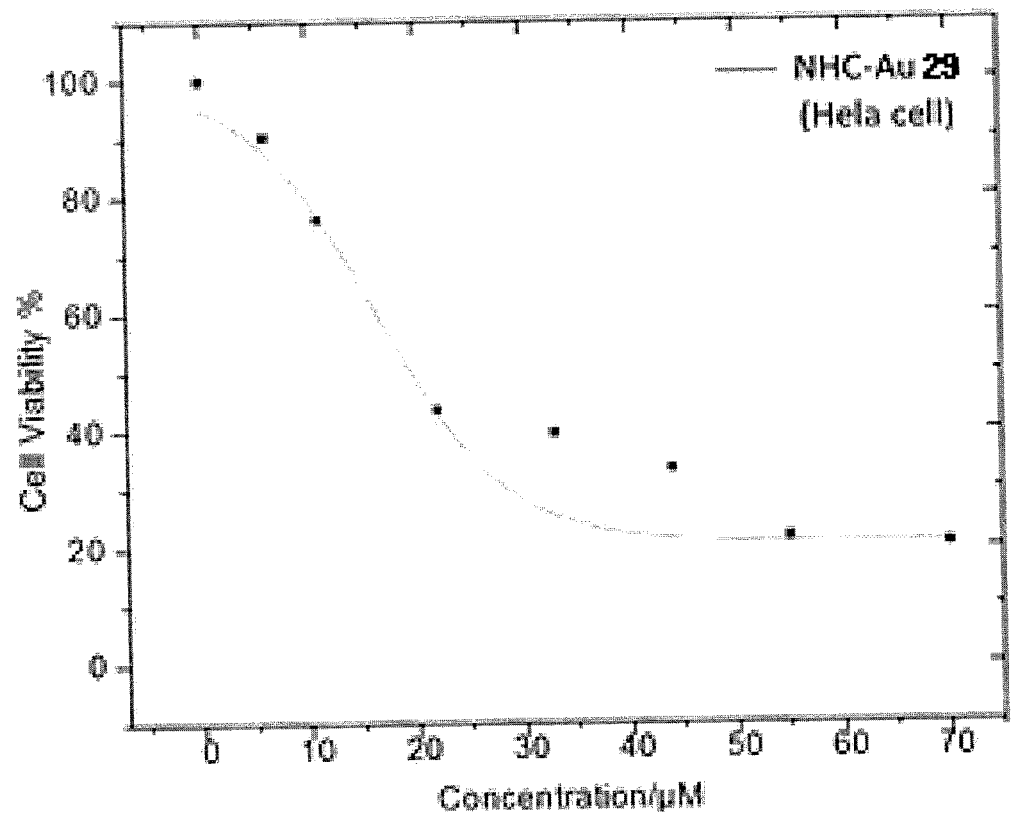
FIG. 25D is a plot of the cell viability vs concentration for the MTS assay of complex 29 with Hela cell line. $IC_{50}=18.8\pm0.77$ μM.
Figure 25E:
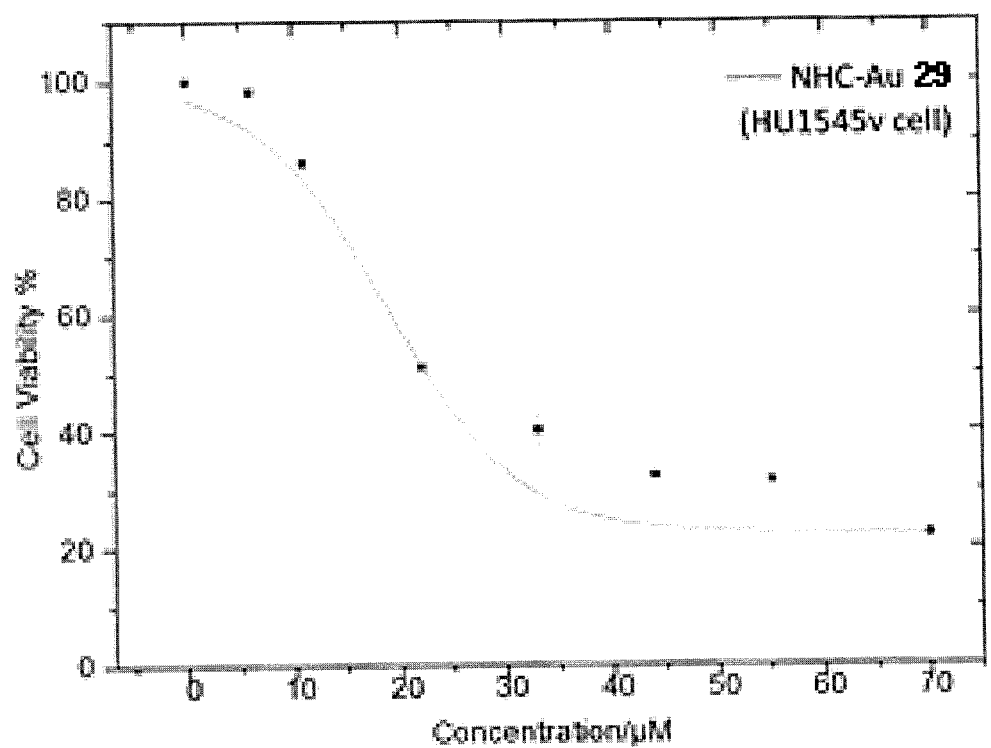
FIG. 25E is a plot of the cell viability vs concentration for the MTS assay of complex 29 with HU1545v cell line. $IC_{50}=22.3\pm1.41$ μM.
Figure 25F:
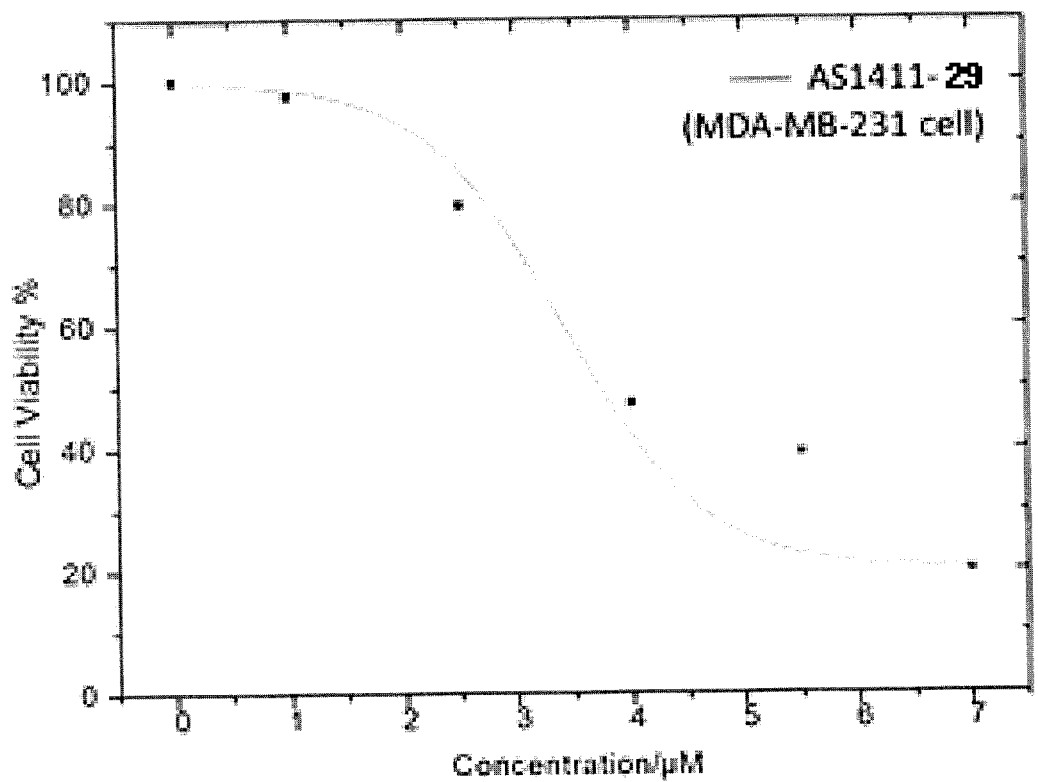
FIG. 25F is a plot of the cell viability vs concentration for the MTS assay of conjugate 32 (AS1411-29) with MDA-MB-231 cell line. $IC_{50}=3.77\pm0.81$ μM.
Figure 25G:
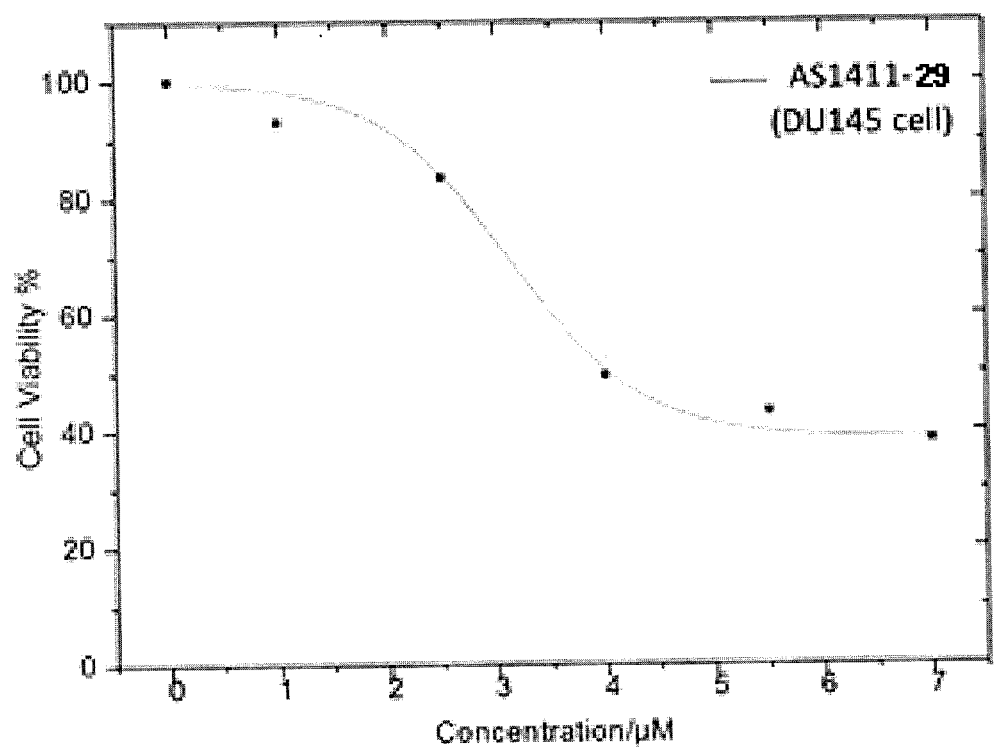
FIG. 25G is a plot of the cell viability vs concentration for the MTS assay of 32 (AS1411-29) with DU145 cell line. $IC_{50}=3.92\pm0.70$ μM.
Figure 25H:
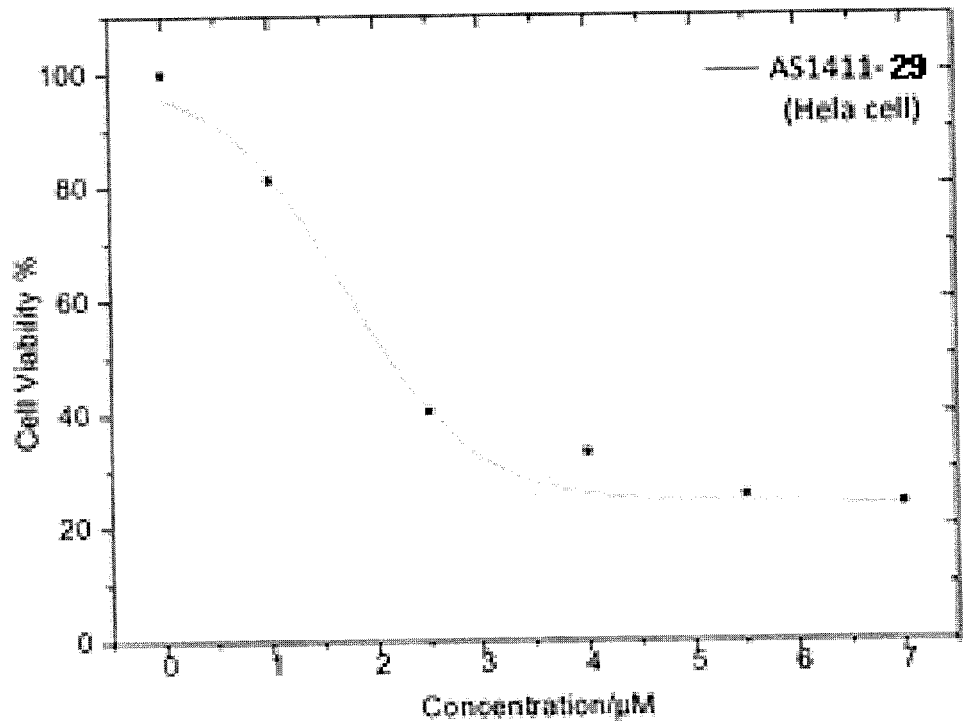
FIG. 25H is a plot of the cell viability vs concentration for the MTS assay of 32 (AS1411-29) with Hela cell line. $IC_{50}=2.04\pm0.16$ μM.

A cell viability assay to measure the cytotoxicity of the aptamer-drug conjugate 21 and aptamer-ligand conjugate 28 were performed, as indicated in FIG. 13. The aptamer-drug conjugate 21 efficiently killed 50% CCRF-CEM cells in 24 h at a concentration of 600 nM, which is a much higher efficiency than complex 19. The $IC_{50}$ for the aptamer-ligand conjugate 28 is only 1200 nM. MTS assays were conducted as follows. For CCRF-CEM and K562 cells, 100 µL of 30000 freshly collected cells were seeded into each well of a 96-well plate, and then incubated with different concentration of the tested compound. After 4 h of incubation, the mixture was centrifuged and 80 µL of old media was removed from each well. Then, 200 uL of fresh media was added to each well for another 48 h incubation under at 37° C. in a 5% $CO_2$ atmosphere. For the other adherent cells (MDA-MB-231, HeLa, PC-3 DU145, HEK293, HU1545v), cells were suspended in medium and were seeded into 96-well plates and cultured for 24 h. The medium was replaced with fresh medium (no fetal bovine serum) containing the free NHC—Au drug or the prepared aptamer-drug conjugate at different concentrations. Cells were further cultured for 4 hours to allow the uptake of the drug and aptamer drug conjugate. After which, cells were washed twice with PBS and fresh medium were added for another 48-hours incubation. For all the cells, after 48 h incubation, the mixture in each well was centrifuged to remove all the supernatant, and then each well was treated with 100 uL of MTS dye (MTS=3-(4,5-dimethylthiazol-2-yl)-5-(3-carboxymethoxyphenyl)-2-(4-sulfophenyl)-2H-tetrazolium) diluted with fresh media with no phosphatidyserine. The assay was allotted 2 h at 37° C. for development, and then the 490 nm absorbance of each well was collected on a Tecan plate 110 reader. Each cell measurement had the treatment background subtracted before analysis. Cells in media and DMSO (0.01%) alone were used as a control. The $IC_{50}$ values were calculated as the concentrations reducing proliferation of untreated control cells by 50% and are given as the means and errors of 2-3 independent experiments. FIG. 19A-19B shows an MTS assay of complex 27 and conjugate 30 with CCRF-CEM cell lines, and of complex 27 with K562 cell line. FIG. 20 compares the cytotoxicity between NHC—Au complexes 19 and 27 and their corresponding conjugates 21 (sgc8c-19) and 30 (sgc8c-27). The MTS cell proliferation assay results demonstrate the specific cytotoxicity of complex 29 and its conjugate 31 (sgc8c-29) towards CCRF-CEM cells CCRF-CEM and K562 cells is shown in FIG. 22. FIG. 23 tabulates MTS cell proliferation assay results of cancer cell lines and normal cell lines after treated with cationic NHC—Au complex 29 and 32 (AS1411-29) conjugate. AS1411 aptamner was used as a control. The cytotoxicity of complex 29 is greatly improved (>6 fold) after conjugated to the nucleolin targeted aptamer AS1411. FIGS. 24A and 24B indicates cell viability of MDA-MB-231, HU1545 and HEK293 after incubation with NHC—Au complex 29 and conjugate 32 (AS1411-29). FIGS. 25A-25E show the results of the MTS assay of complex 29 with MDA-MB-231, DU145, HEK293, Hela, and HU1545v cell lines, respectively. FIGS. 25F-25H show the results of the MTS assay of conjugate 32 (AS1411-29) with MDA-MB-231, DU145, Hela cell lines, respectively.

Flow Cytometry Analysis was conducted as follows. Cells were plated in a 35 mm cell culture dish (Corning Incorporated, Corning, N.Y., USA) and grown to around 80% confluency for 24 h before the experiments. Cells were washed twice with 1 mL PBS and then incubated with the prepared aptamer-drug conjugate and LIB-drug conjugate at the concentration of 250 nM for 2 h at 4° C. After incubation, cells were washed with washing buffer three times, dispersed in 80 µL binding buffer, and finally subjected to flow cytometry analysis using a FACScan cytometer (Becton Dickinson Immunocytometry Systems, San Jose, Calif., USA). Fluorescence was determined by counting 30,000 events, and data were analyzed with FlowJo software.

Figure 26A:
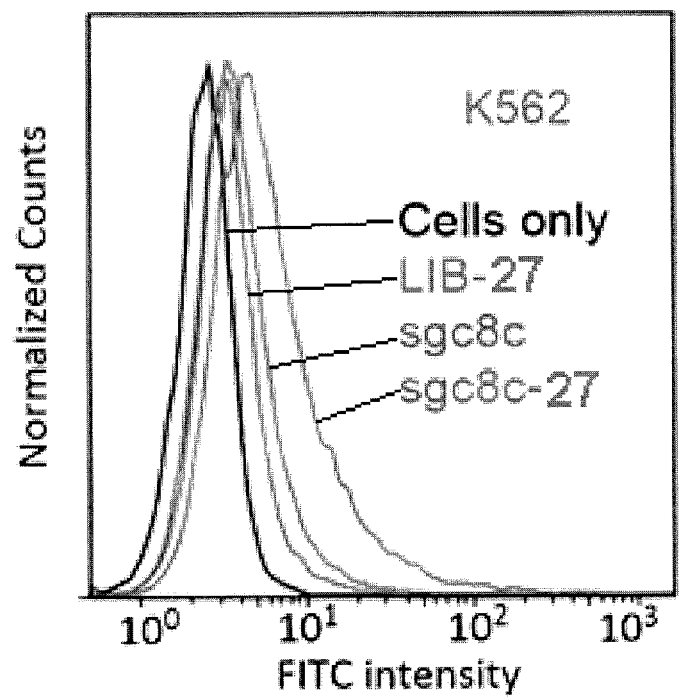
FIG. 26A shows plots of normalized counts vs. FITC intensities for flow cytometry assays of conjugate 30 (sgc8c-27) with the K562 cell line.
Figure 26B:
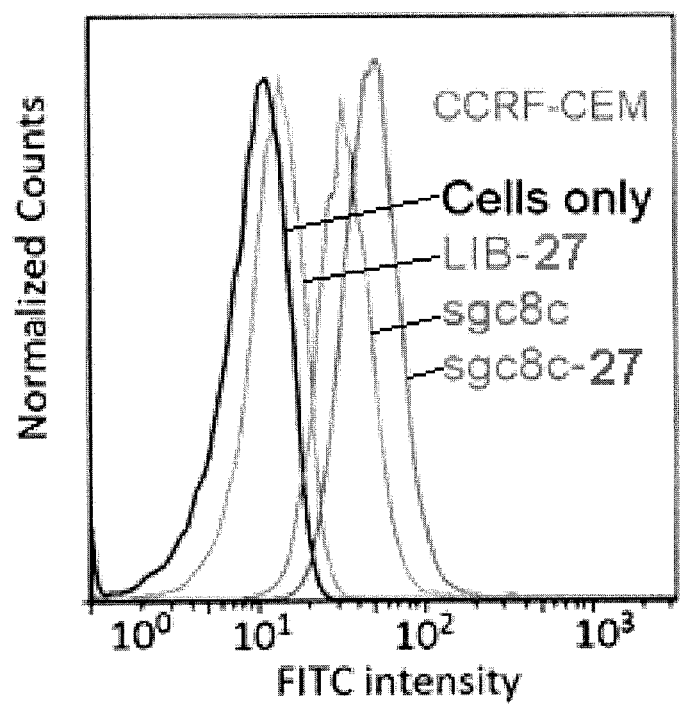
FIG. 26B shows plots of normalized counts vs. FITC intensities for flow cytometry assays of conjugate 30 (sgc8c-27) with the CCRF-CEM cell line.
Figure 27A:
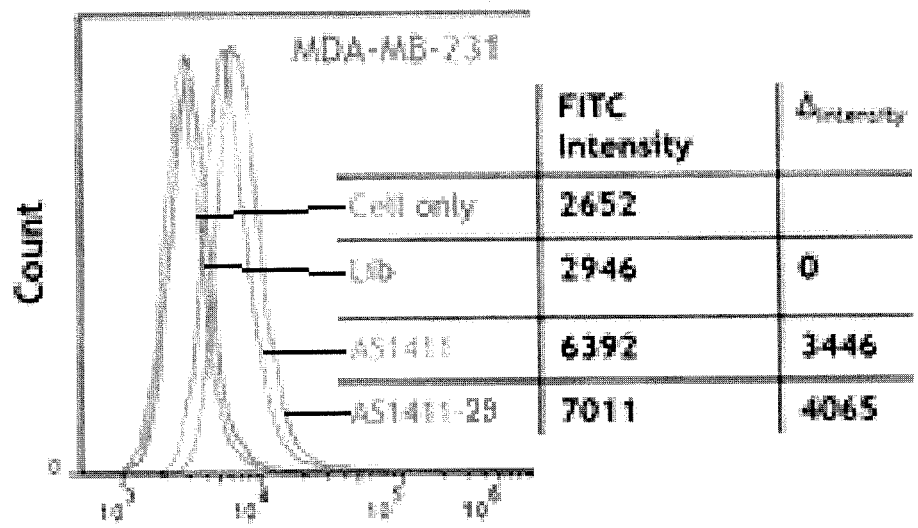
FIG. 27A shows plots of normalized counts vs. FITC intensities for flow cytometry analysis of MDA-MB-231 cells after incubation with 32 (AS1411-29).
Figure 27B:
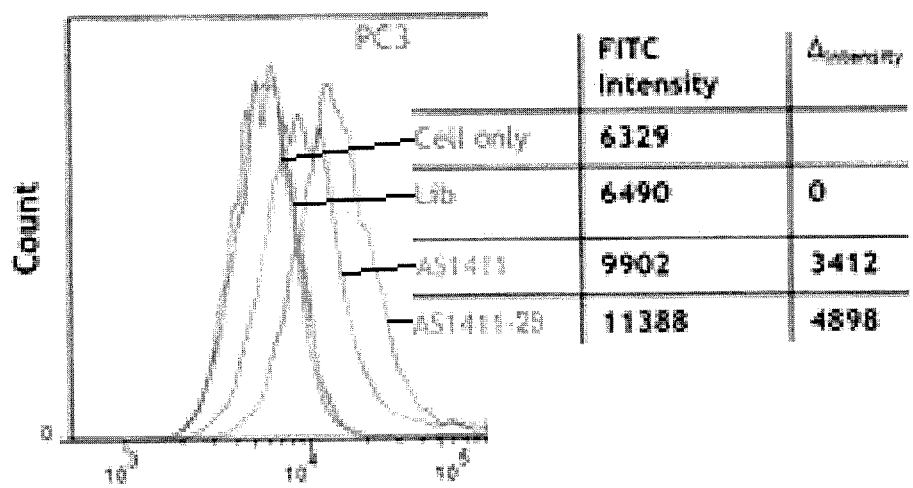
FIG. 27B shows plots of normalized counts vs. FITC intensities for flow cytometry analysis of PC3 cells after incubation with 32 (AS1411-29).
Figure 27C:
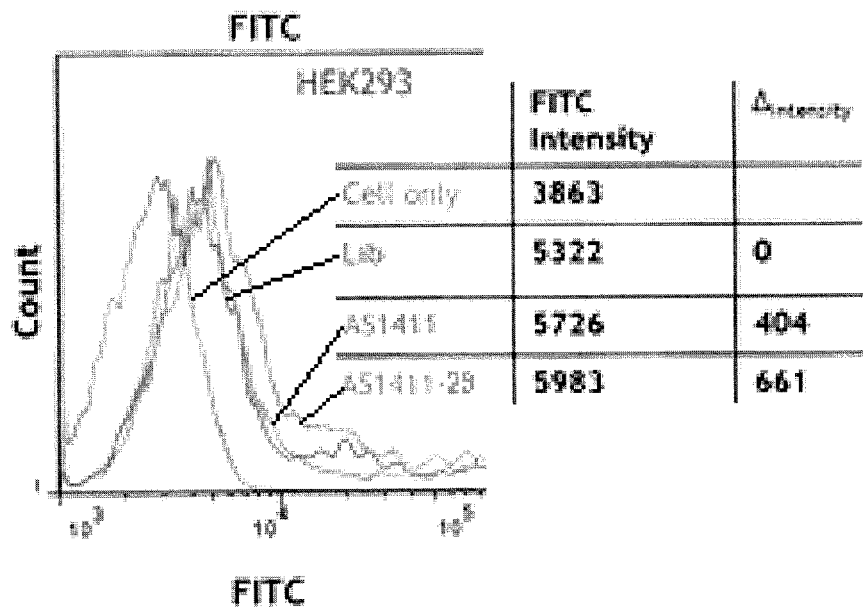
FIG. 27C shows plots of normalized counts vs. FITC intensities for flow cytometry analysis of HEK293 cells after incubation with 32 (AS1411-29).
Figure 27D:
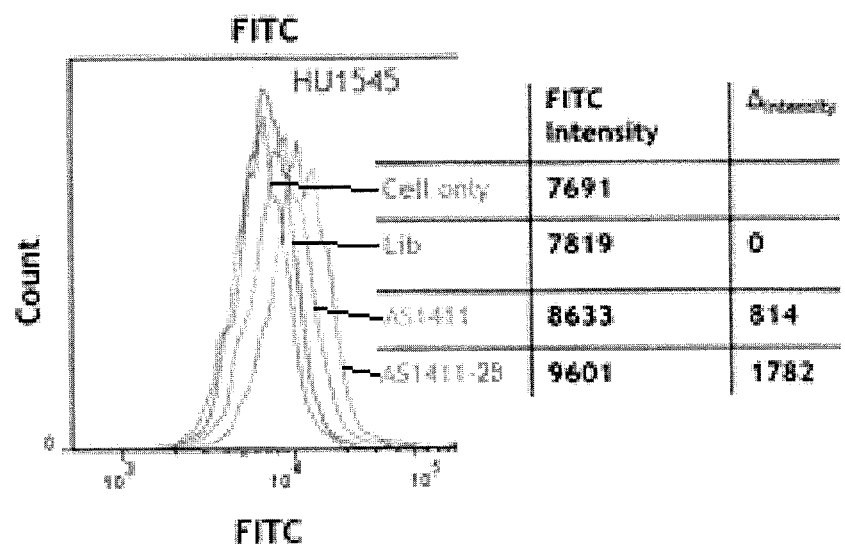
FIG. 27D shows plots of normalized counts vs. FITC intensities for flow cytometry analysis of HU1545 cell after incubation with 32 (AS1411-29).

Flow cytometry assays of conjugate 30 (sgc8c-27) with the K562 cell line (left) and the CCRF-CEM cell line are shown in FIGS. 26A and 26B, respectively. Random aptamer sequences conjugated to 27 to create LIB-27 were used as negative control. CCRF-CEM cells incubated with aptamer sgc8c and the conjugate 28, which can target CCRF-CEM cells exhibit fluorescence intensity increases. In Similar manner, flow cytometry analysis of MDA-MB-231 cell, PC3 cell, HEK293 cell and HU1545 cell, FIGS. 27A-27D, respectively, after incubated with 32 (AS1411-29) were conducted. AS1411 aptamer was used as positive control, and random library sequences was used as negative control. Target cell MDA-MB-231 and PC-3 show much higher enhancement of fluorescence intensity than the normal cell HEK293 and HU1545 cells.

Figure 28A:
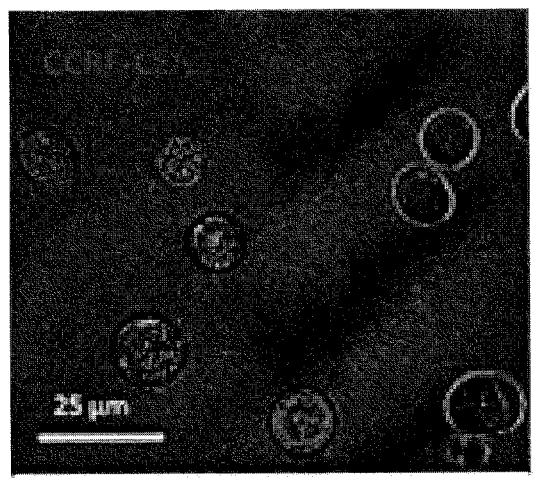
FIG. 28A shows a confocal microscopy image of CEM cells incubated with 30 (sgc8c-27) labelled with fluorescein.
Figure 28B:
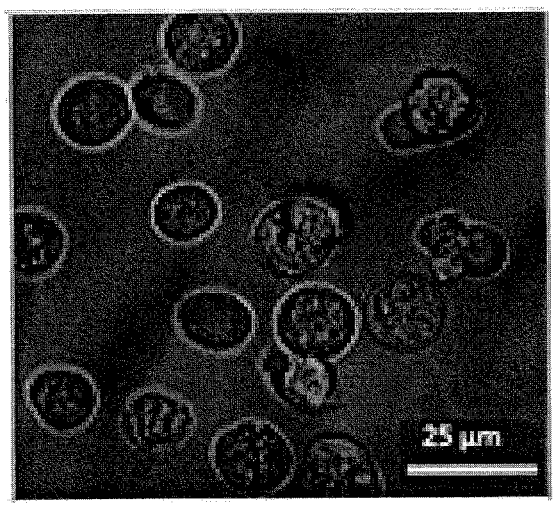
FIG. 28B shows a confocal microscopy image of CEM cells incubated with LIB-27 labelled with fluorescein.
Figure 28C:
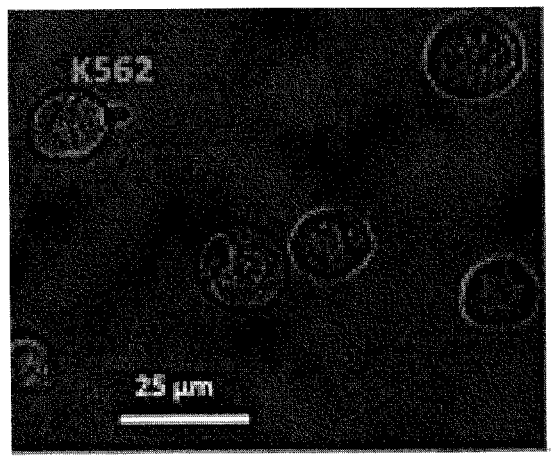
FIG. 28C shows a confocal microscopy image of K562 cells incubated with 30 (sgc8c-27) labelled with fluorescein.
Figure 28D:
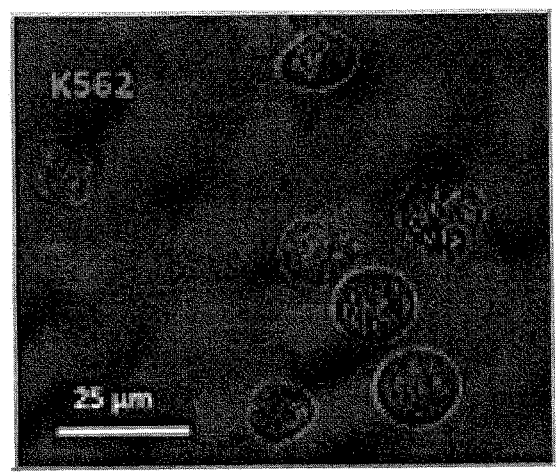
FIG. 28D shows a confocal microscopy image of K562 cells incubated with LIB-27 labelled with fluorescein.
Figure 29A:
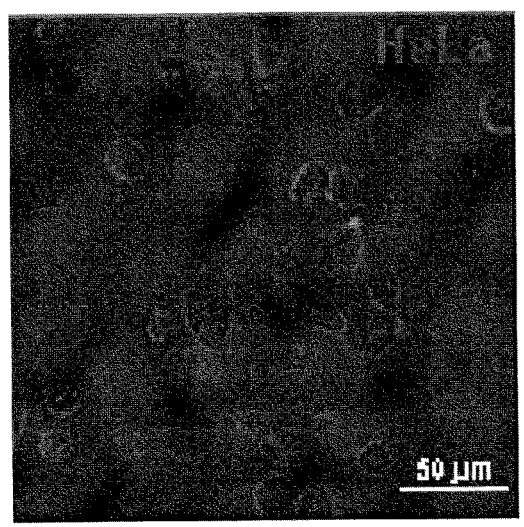
FIG. 29A shows a confocal microscopy images of HeLa cells treated with 32 (AS1411-29) labelled with fluorescein.
Figure 29B:
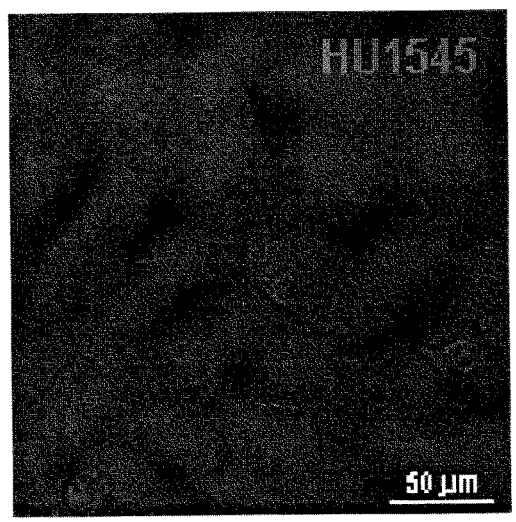
FIG. 29B shows a confocal microscopy images of HU1545 cells treated with 32 (AS1411-29) labelled with fluorescein.

Confocal microscopy was carried out with cellular fluorescent images collected on a Leica TCS SP5 confocal microscope (Leica Microsystems Inc., Exton, Pa.) with a 63× oil immersion objective and Leica Confocal Software. Cells were treated with 500 nM aptamer-drug conjugate or LIB-drug conjugate, respectively, in serum-free cell culture medium, incubated in a cell culture incubator for 2 h, followed by washing with Dulbecco's PBS. The resultant cells were then observed by confocal microscopy. FIG. 28A shows the confocal microscopy images of CEM cells incubated with 30 (Sgc8c-27) for 4 h at 37° C. where the Sgc8c aptamer and LIB sequences were labelled with fluorescein and FIG. 28B is that of CEM cells incubated by the same procedure with LIB-27. In like manner, confocal microscopy images of K562 cells incubated with 30 (Sgc8c-27) and LIB-27 are shown in FIGS. 28C and 28D, respectively. Only the cells treated with 30 exhibit appreciable internalization of the conjugate. In Similar manner confocal microscopy images of HeLa cells and HU1545 cells treated with 32 (AS1411-29) at 500 nM for 2 hours are indicated in FIGS. 29A and 29B, respectively, where internalization of the conjugate is indicated.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

metal complex or the bis-N-heterocyclic-carbene metal complex comprises at least one N-heterocyclic-carbene of the structure:

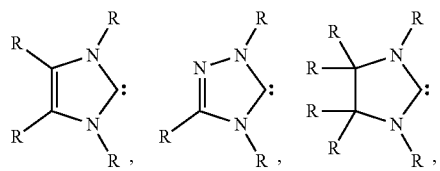

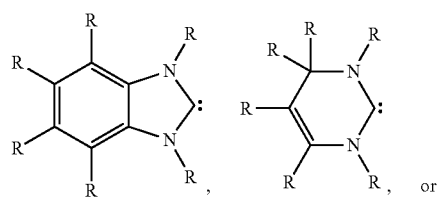

or

---

---

We claim:

1. An aptamer-N-heterocyclic-carbene metal complex conjugate (aptamer-NHCM conjugate), comprising:
   an aptamer;
   at least one N-heterocyclic-carbene metal complex (NHCM) or bis-N-heterocyclic-carbene metal complex (bis-NHCM): and
   a coupling unit, wherein the coupling unit comprises a hydrolytically stable bond between the aptamer and the at least one NHCM or bis-NHCM.

2. The aptamer-N-heterocyclic-carbene metal complex conjugate of claim 1, wherein the N-heterocyclic-carbene metal complex or bis-N-heterocyclic-carbene metal complex comprises a metal selected from Au, Ag, Pt, Pd, Ru, Ni, or Cu.

3. The aptamer-N-heterocyclic-carbene metal complex conjugate of claim 1, wherein the N-heterocyclic-carbene -continued

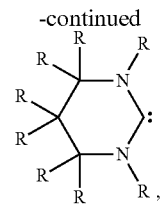

wherein R-groups are independently H, $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene and optionally substituted or multiply substituted with any of Cl, Br, I, F, OH, R'$_2$N, R'SO$_2$, R'SO, R'S, R'$_3$Si, R'O, NH$_2$, C(O)OH, N$_3$, C≡CH, vicinal disubstituted with C(O)OC(O), a cyclic conjugated diene, any salts derived therefrom or any condensation or addition derivative substituent therefrom, wherein R' can be $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene, wherein at least one of the R groups comprises the condensation or addition derivative substituent comprising the coupling unit forming the stable bond between the N-heterocyclic-carbene metal complex and the aptamer, wherein the condensation or addition derivative substituent is derived from condensation or addition of a —NH$_2$ and —C(O)OH, —N$_3$, and —C≡CH; —NH$_2$ and vicinal disubstituted —C(O)OC(O)—, or homocyclic or heterocyclic conjugated diene and —C≡CH or —HC═CH$_2$, wherein R and R' groups are linear, branched, cyclic, polycyclic or any combination thereof, and wherein the N-heterocyclic-carbene is achiral, a racemic mixture, partially resolved enantiomer, resolved enantiomer, resolved diastereomers, or a mixture of diastereomers.

4. The aptamer-N-heterocyclic-carbene metal complex conjugate of claim 1, wherein the bis-N-heterocyclic-carbene metal complex further comprises a framework that positionally fixes the relative proximity and orientation of the N-heterocyclic carbenes of the bis-N-heterocyclic-carbene metal complex.

5. The aptamer-N-heterocyclic-carbene metal complex conjugate of claim 4, wherein the framework and N-heterocyclic carbenes comprise a trans-9,10-dihydro-9,10-ethanoanthracene-11,12-di-oligomethylene-N-heterocyclic-carbene:

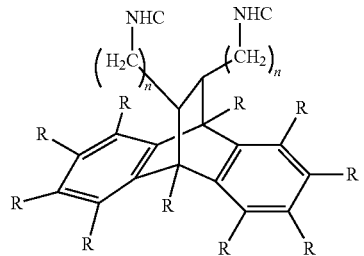

where NHC is an N-heterocyclic carbene, wherein the N-heterocyclic carbenes are independently selected from:

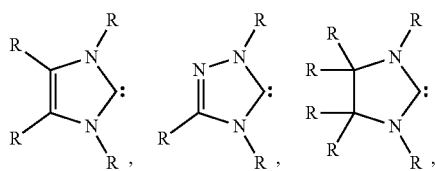

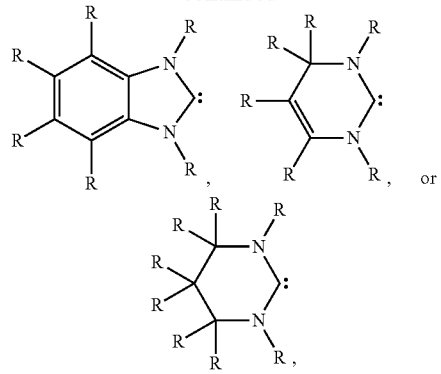

wherein n is 1 to 4, R-groups are independently H, $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene and optionally substituted or multiply substituted with any of Cl, Br, I, F, OH, R'$_2$N, R'SO$_2$, R'SO, R'S, R'$_3$Si, R'O, NH$_2$, C(O)OH, N$_3$, C≡CH, vicinal disubstituted with C(O)OC(O), a cyclic conjugated diene, any salts derived therefrom or any condensation or addition derivative substituent therefrom, wherein R' can be $C_1$-$C_{18}$ alkyl, $C_2$-$C_{18}$ alkenyl, $C_2$-$C_{18}$ alkynyl, $C_6$-$C_{14}$ aryl, $C_7$-$C_{18}$ arylalkyl, $C_8$-$C_{18}$ arylalkenyl, $C_8$-$C_{18}$ arylalkynyl, $C_1$-$C_{18}$ alkoxy, $C_6$-$C_{14}$ aryloxy, $C_7$-$C_{18}$ arylalkyloxy, $C_2$-$C_{18}$ alkenyloxy, $C_2$-$C_{18}$ alkynyloxy, $C_8$-$C_{18}$ arylalkenyloxy, $C_8$-$C_{30}$ arylalkynyloxy, $C_2$-$C_{30}$ alkylester, $C_7$-$C_{15}$ arylester, $C_8$-$C_{30}$ alkylarylester, $C_3$-$C_{18}$ alkenylester, $C_3$-$C_{18}$ alkynylester, $C_3$-$C_{18}$ di- or poly-ether, $C_3$-$C_{18}$ di- or poly-etherester, $C_3$-$C_{18}$ di- or poly-ester, $C_3$-$C_{18}$ di- or poly-amine, $C_4$-$C_{18}$ di- or poly-ene, wherein one of the R groups of the bis-N-heterocyclic-carbene and framework comprises the condensation or addition derivative substituent comprising the coupling unit forming the stable bond between the N-heterocyclic-carbene metal complex and the aptamer, wherein the condensation or addition derivative substituent is derived from condensation or addition of a —NH$_2$ and —C(O)OH, —N$_3$, and —C≡CH; —NH$_2$ and vicinal disubstituted —C(O)OC(O)—, or homocyclic or heterocyclic conjugated diene and —C≡CH or —HC═CH$_2$, wherein R and R' groups are linear, branched, cyclic, polycyclic or any combination thereof, and wherein the N-heterocyclic-carbene is achiral, a racemic mixture, partially resolved enantiomer, resolved enantiomer, resolved diastereomers, or a mixture of diastereomers.

6. The aptamer-N-heterocyclic-carbene metal complex conjugate of claim 1, further comprising a fluorescent or phosphorescent dye attached to the at least one N-heterocyclic-carbene metal complex (NHCM) or bis-N-heterocyclic-carbene metal complex (bis-NHCM).

7. The aptamer-N-heterocyclic-carbene metal complex conjugate of claim 1, wherein the aptamer-NHCM conjugate is 1-(anthracen-9-ylmethyl)-3-(4-N-sgc8c-aptamer-carbamoylbenzyl)benzo[d]imidazolium gold(I) chloride, 1-(methyl)-3-(4-N-sgc8c-aptamer-carbamoylbenzyl)benzo[d]imidazolium gold(I) chloride, 1-(anthracen-9-ylmethyl)-3-(4-N-sgc8c-aptamer-carbamoylbenzyl) benzo[d]imidazolium triphenylphosphino gold(I) tetrafluoroborate, or 1-(anthracen-9-ylmethyl)-3-(4-N-AS1411-aptamer-carbamoylbenzyl) benzo[d]imidazolium triphenylphosphino gold(I) tetrafluoroborate.

8. The aptamer-N-heterocyclic-carbene metal complex conjugate of claim 1, wherein the aptamer binds to a cancer cell specific receptor.

9. The aptamer-N-heterocyclic-carbene metal complex conjugate of claim 8, wherein the cancer cell specific receptor is a G-protein coupled receptor, an epidermal growth factor receptor, an epidermal growth factor tyrosine kinase receptor mutation variant III, or a protein tyrosine kinase receptor 7.

10. The aptamer-N-heterocyclic-carbene metal complex conjugate of claim 1, wherein the aptamer-N-heterocyclic-carbene metal complex further comprises at least one bond between a metal of the N-heterocyclic-carbene metal complex and an ion or ligand, wherein the ions or ligands independently comprise Cl, Br, I, OH, Cl$^-$, Br$^-$, I$^-$, $BF_4^-$, $PF_6^-$, $SbF_6^-$, $^-OSO_2CF_3$, or $^-OSO_2C_6H_5$.

11. The aptamer-N-heterocyclic-carbene metal complex conjugate of claim 1, wherein a portion of the coupling unit comprises an amide —NHC(O)—, a 1,4-substituted triazole —$N_3C_2H$—; an imide [—C(O)]$_2$N—, a bicycle[2.2.1]heptane —$C_7H_8$—, a substituted bicycle[2.2.1]heptane, a 7-oxabicyclo[2.2.1]heptane —$C_6H_6O$—, a substituted 7-oxabicyclo[2.2.1]heptane, a 7-azabicyclo[2.2.1]heptane —$C_6H_7N$—, a substituted 7-azabicyclo[2.2.1]heptane, or a succinimide thioether.

12. The aptamer-N-heterocyclic-carbene metal complex conjugate of claim 1, wherein the aptamer is capable of binding to a specific cell surface receptor present on a target cell.

13. The aptamer-N-heterocyclic-carbene metal complex conjugate of claim 12, wherein the target cell is a cancer cell and the specific cell surface receptor is present on the surface of the cancer cell.

14. The aptamer-N-heterocyclic-carbene metal complex conjugate of claim 1, wherein the NHCM is conjugated to the aptamer in a covalent manner.

15. The aptamer-N-heterocyclic-carbene metal complex conjugate of claim 1, wherein the aptamer is conjugated to the NHCM in a non-covalent manner.

16. A method of treating cancer or a microbial infection, comprising administering to a subject in need thereof, a pharmaceutically effective amount of the aptamer-N-heterocyclic-carbene metal complex conjugate of claim 1.

17. The method of claim 16, wherein the aptamer-N-heterocyclic-carbene metal complex conjugate binds to the disease causing cells via the specific cell surface receptor present on the disease causing cells.

18. The method of claim 16, wherein the subject is a mammal selected from the group consisting of a human, a porcine, a canine, a rodent, a feline, and a bovine.

* * * * *